United States Patent
Estes et al.

(10) Patent No.: US 7,423,135 B2
(45) Date of Patent: Sep. 9, 2008

(54) β-ACTIN AND RPS21 PROMOTERS AND USES THEREOF

(75) Inventors: Scott D. Estes, Framingham, MA (US); Weiqun Zhang, Southborough, MA (US)

(73) Assignee: Genzyme Corporation, Cambridge, MA (US)

( * ) Notice: Subject to any disclaimer, the term of this patent is extended or adjusted under 35 U.S.C. 154(b) by 275 days.

(21) Appl. No.: 10/874,242

(22) Filed: Jun. 24, 2004

(65) Prior Publication Data

US 2005/0026252 A1 Feb. 3, 2005

Related U.S. Application Data

(60) Provisional application No. 60/480,768, filed on Jun. 24, 2003.

(51) Int. Cl.
  *C07H 21/02* (2006.01)
  *C07H 21/04* (2006.01)
  *C12N 5/00* (2006.01)
  *C12N 5/02* (2006.01)
  *C12N 5/06* (2006.01)
  *C12N 5/10* (2006.01)
  *C12P 21/06* (2006.01)

(52) U.S. Cl. ............... 536/23.1; 536/24.1; 435/325; 435/358; 435/359; 435/69.1

(58) Field of Classification Search ............ 536/23.1, 536/24.1; 435/325, 358, 359, 69.1
See application file for complete search history.

(56) References Cited

OTHER PUBLICATIONS

Singh et al., Recombinant expression systems for allergen vaccines. Inflamm Allergy Drug Targets. 5(1): 53-9, 2006.*
Gettemans et al. Nuclear actin-binding proteins as modulators of gene transcription. Traffic. 6(10): 847-57, 2005.*
Wei et al., Post-transcriptional regulation of opioid receptors in the nervous system. Front Biosci. 9: 1665-79, 2004 (one page abstract from PubMed).*
Niwa et al., Efficient selection for high-expression transfectants with a novel eukaryotic vector. Gene. 108(2): 193-9, 1991.*
Batra et al., Expression of the human MUC1 mucin cDNA in a hamster pancreatic tumor cell line HP-1. Int J Pancreatol. 12(3): 271-83, 1992.*
Davidson, The genetics of TBP and TBP-related factors, Trends Biochem Sci. 28(7):391-8, 2003.*
Sugiyama et al. Strong transcriptional promoter in the 5' upstream region of the human beta-actin gene. Gene. 65(1): 135-9, 1988.*
Kornberg, The molecular basis of eukaryotic transcription. Proc Natl Acad Sci U S A. 104(32): 12955-61, 2007.*
Partial International Search Report, International Application No. PCT/US2004/017422, mailed Jan. 13, 2005.
Beddington et al., "An In Situ Transgenic Enzyme Marker for the Midgestation Mouse Embryo and the Visualization of Inner Cell Mass Clones During Early Organogenesis," *Develop., Co. Biologists, Cambridge, GB*, 106:37-46 (1989).
Breitbart et al., "Gene-Enhanced Tissue Engineering: Applications for Wound Healing Using Cultured Dermal Fibroblasts Transduced Retrovirally with PDGF-B Gene," *Annals Plastic Surg.*, 43:632-639 (1999).
Elder et al., "Evidence that the Functional Beta Actin Gene is Single Copy in Most Mice and is Associated with 5' Sequences Capable of Conferring Serum and Cycloheximide-Dependent Regulation," *Mol. Cell. Biol.*, 8:480-485 (1988).
Kim et al., "Gene Transfer in Bovine Blastocysts Using Replication-Defective Retroviral Vectors Packaged with Gibbon Ape Leukemia Virus Envelopes," *Mol. Reproduction Develop.*, 35:105-113 (1993).
Nakajima-Iijima et al., "Molecular Structure of the Human Cytoplasmic Beta Actin Gene Interspecies Homology of Sequences in the Introns," *PNAS*, 82:6133-6137 (1985).
Nudel et al., "The Nucleotide Sequence of the Rat Cytoplasmic Beta-Actin Gene," *Nuc. Acids Res.*, 11:1759-1771 (1983).
Nudel et al., The Nucleotide Sequence of the Rat Cytoplasmic Beta-Actin Gene, *EBI Database Accession No.* V01217 (1983).
Stahlbom et al., "Isolation and Characterization of the Beta Actin Gene from Chinese Hamster," *EBI Database Accession No.* U20114 l(1995).
Written Opinion of the International Searching Authority, International Application No. PCT/US2004/017422, mailed Mar. 29, 2005.

* cited by examiner

*Primary Examiner*—Valerie Bertoglio
*Assistant Examiner*—Wu-Cheng Winston Shen
(74) *Attorney, Agent, or Firm*—Finnegan, Henderson, Farabow, Garrett & Dunner, LLP

(57) ABSTRACT

The invention relates to isolation of novel β-actin and ribosomal protein S21 (rpS21) promoters and uses thereof. In particular, this invention features nucleotide sequences for rodent β-actin promoters including, hamster, rat, and mouse, and hamster rpS21 promoter.

17 Claims, 15 Drawing Sheets

```
HAMSTER 487  TGTGGGAACCACAGAGTAGCCCTGAACGTGGGGGTGTGCTTCCAGTATACT---CTGGG-G
             ||||||||||||||||||||||||||||||||||||||||||||||||||||   |||| |
RAT       1  TGTGGGAAAGATAAAGTCGCTCTGAACCTGGGGGTGTGTTTCCAGTATGCTGGAGTGGTG

GTCACCCTTTCCATACTGGAGGCCTCTGCAACTTCAAAAATGCTCTGCTACCAA-CCTAGC
             ||||||||||||||||||||||||||||||||||||||||||||||||||||||| |||||
             GTCACCCTTTCCAGACTGGAGGCCTCTGCAACTTCAAAAATGCCCTGCCAC-AAGCCTAGA

ACAAGGAAGTTGGTCCAGCCTCCCCACGCAGGGCCACTGCTGCAGTCCATATATGGACT-
             |||||||||||||||||||||||||||||||||||||||||||  |||||||||||||
             ACAAGGAAGCTGGTCCAGCCTCCCCATGCACAGCCACTG-T--AGCCCATATATGGA-TG

AAGCCTTCCTTGGTTTCAACACCTACACTCACTGAGCC----C-C---TACTATGTGTAT
             |||||||||||||||||||||||||||||||||||||     | |   |||||||||||
             AAGCCTTCCTTGGTTTCAACACCTACACTTTGTGAGCCAGTGCACACCTACTATGCATGT

GCAGAGCCGA-GACAGGCCC-GAGCATCTCATCTGAAGCACCCCTTCTTGCCTAAAT-TCA
             ||||||||   ||||||||  |||||||||||||||||||||||||||||||||| |
             GTAAAGCC-ATGGCAGTCCAGAGCATCCCACCTGAAGCATTCTCCTTGCCTAAATAT-A

GTTTTCTGTCACTTTCTCCCAGGAGGTGTGTCCCTCTAAGCTAAGCC-AGGGGTCCCT
             |||||||||||||||||||||||||||||||||||||||||||||||  |||||||||
             GCTTTCTGTCACTCTCTCCCAGGAGTTGTGCGTCCTTCTAAGCTAAGCTGAGGGA-CCCG

CACCCCCTGCCCCACTCCCATCCC-TAG-TGTAGGTATCAGCTGAA-G----AGCTTCCTGA
             ||||                    ||| ||||||||||||||||  |    ||||||||||
             -ACCC-T-CA--ACTCTGATCCCCT-GCTGTAGCTATCAGCCAAATGGCTAGCTTCCTGA

GCAGAACACTC  893
             |||||| ||||
             GCAGAACTCTC  417
```

FIG. 1A

```
HAMSTER 1047  ACAGTTCGGCTGTGGCTGCACATAACTA-ACAGAGGATAGATGGTGGG-TCCCAGCCCAA
               ||||||||  |||||||||||||||||| ||| ||||| | |||||||| |||||||||
RAT     546   ACAGTTCAGCTGTGGCTGCACATAA-TACATAGAGGCTAGATGGTGGGCT-CCAGCCCAA

C-AGTGCCTGGCAATCACCCAGAGCCACCAGAGCCTAACGGCCTTGGCTTAGTTTTTGCCTG
               |  ||| |||| ||||||||||||| |||||||||||||| ||||||||||   |||||
              CGA-TGCCTGGCAGTCACCCAGAGCCACTAGCTAACGGCCTAGCCCAGGCTTAG--TCTTGCCTG

GGTGTGATCAGGCAGCCCCTCCAAAACTGCCCGGACTCCATGACAAGTTTTGCTTGTTCTA
              ||||||||||||||||||||||||||| |||||||||||||||| |||||||||||||| 
              GGTGTGATCAGGCAGCCCCTCCAAAAGTG-CCGGACTCCATGAGAAGTTTTGCTTGTTCGA

TAGAGCACAGTTCCTTTCTAGTCTGGGGCAAG-GGACATCGGGAGACATCTTCCTG---
              | ||||||||||||| ||||||||||| ||| |||||||  |||||||||||||| 
              TTGAGCACAGTTCCTTTCTAGTCCGGGGC-AGAGGATATCTGGAGGCATCTTCCTGCAA

C-AACAGCTCCAGTCACTGGACCACC-AGGCTCGCCCCTGTCTTTGGTGTGTGGCCCTGAG
               | ||| |||||||||||||||||| ||||||||||||||| |||  ||| |||||| |
              CAAACACCTCCAGTCACTGGACCACCGGGACCACCGGGCTTGCCCTATC-CT--TG-G-GACTCTG-G

TCTCCTAAGTGGCCCAA-A-CCTGTGAAGACCCCT-CCAACCACAGTTTTGCTTCTAAAT
               |   ||||| || ||| | |||||||  || || |||| ||||||||||||| ||||
              -C-CTTGAGTGG-TCAAGATCC-CTGAAGA-CCTTCCCAACCACCAGTCTCTGCTTCCAAGT

TGTACCCCAACACACCTAGCAAATT-GAAACCCCACCAGAAGTCCCCCAGATCTGGCTTT
              |||||||||||||||||||||||| ||| ||||||||||||| |||||||||||||||
              TGTACCCCAACACACCTAGCAAATTAG-AACTGCAGCAGAGAAGGCCCCCAGATCTGGCTTT
```

FIG. 1B

```
CC-GGCTATTGCTGGCAAGGGGGAGTGACTCCCGGCCCATTCAATCCAGGCCCCCGCGTGT
   |||  ||||||||||||||||| |||||||||||||||  |||||||||||||||||||
   ||| —||||||||||||||||| ||||||||||||||| —|||||||||||||||||||
CCTGACTATTGCTAGCAAGGGGGAGTGACTGCTCTCTGCCCATTCAATCCAGACCCCGTGT

TCCTCAAACAAGAA-GCCACGT-AAACATAAACCGAGCCTCCATGCTGACCCTTGCCCA-
||||||||||||||  |||||| |  ||| |||||
|||||||||| ||| —|||||| —|  ||| ||||| — — — — — — — — — — — —
CCCTCAAACAA-AAGGCCAC-TCAAATAGGGTCCGGGCCTTCAAGCTGACCCTCGCCCAC

TCGAGGT-ACTCAATGTTCACGTGATATCCACACCCAGAGGGTCCTGGGGTGGGTGCATG
||| ||| |||||||||||| |||| ||||||||||||||||||||||||||||||| ||
||| ||| ||||||||||||—|||| |||||||||||||||||||||||||||||||—||
T-TAGGTGA-TCATTATTCCCGTGACATCCACACCCAGAGGGTCCTGGGGTGGGTGGGTG

AGCCCCAGAATGCAGG-CTTGATAACCGAGACCCTGAATCGGG-CAGTGTCCACAAGGGC
|||||||||||||||| |||||||||||||||||||||||||| ||||||||||||||||
|||||| ||||||||| ||||||||| ||||||||||||||||—||||||||||||||||
ACCCCCAGAATACAGGCCTAG-TAACCGAGTCACTGAAT-GGGATAGTGTCCACAAGGGC

GGAGGCCCAGTCATG---CATGTTCGGGCCTATGGGGCCAGCACCCAACGCCAAAACTCTC
|| |||||| ||||    |||||||||||||  |||||||||||||||||||||  |||||
||—|||||| |||| —— ||||||||||||| —|||||||||||||||||||  —|||||
GG-GGGCTATTCTTGTCCAT-CT-GGGCCTACGGAACCAGCACCCATCGCCC-AAACTCTT

CATCCCTCTTCCTCAATCTCGGCTTTCTCTCT--CT--C------TC-TCTTTTTTTTTT
||||| |||||||||||||| |||||||||||  ||  |      || ||||||||||||
||||| ||||||||||||||—|||||||||||——||——|——————||—||||||||||||
CATCCCTCTTCCTCAATCTC-GCTTTCTCTCTCGCTCGCTTTTTTTCTTCTTCTTTTTTT

TTTATTTTTTTTTGCAAAAGGAGGGGAGAGGGTAAAAAAATGCTGCACTGTGCGG
|||  |||||||||||||||||||| |||||||||||||| |||||||||||||
||| —|||||||||||||||||||| |||||||||||||| |||||||||||||
TTT-TTTTTTTTTTGCAAAAGGAGGGGAGAGGGTAAAAAAATGCTGCACTGTGCGG
```

FIG. 1C

```
CTAGGCCGGTGAGTGAGCGGCGGGAGCCAATCAGCGCTGCGCCGTTCCGAAAGTTGCCTT
-----------------------------------------------------------
CGAGGCCGGTGAGTGAGCGACGCGGAGCCAATCAGCGCCCGCCGTTCCGAAAGTTGCCTT

TTATGGCTCGAGTGGCCGCTGTGGCGTCCTATAAACCCGGCGGGCGCAACGCGCAGCCAC
-----------------------------------------------------------
TTATGGCTCGAGTGGCCGCTGTGGCGTCCTATAAAACCCGGCGGGCGCAACGCGCAGCCAC

TGTCGAGTCCGCGTCCACCCCGGAGCACAGGCCTT-TCGCAGCTCTTTCTTCGCCGCTCC
-----------------------------------------------------------
TGTCGAGTCCGCGTCCACCCCGGAGTACA-ACCTTCTTGCAGCTCCTCCGTCGCCGGTCC

ACACCCCGCCACCAGGTAAGCAGGACAACAGGCCCAGCCGGCCACAGCCCTCCCGTGGGC
-----------------------------------------------------------
ACACCCCGCCACCAGGTAAGCAGGACGTCGGGCCCAGCGGGCCCCAACTTTACCTTGGCC

AGTGACCGCGCTGCAGGGTCGCGGGGACACTC-GGCGCGGACACCGGGGAAGGCTGGAG
-----------------------------------------------------------
ACT-ACCTCGCTGCAGGATCGTGAGGAACACTCAGAAG-GGACACCGTAGAGGGGTGGAG

GGTGGTGCCGGGCCGCGGGAGCGGACACTTTCAGATC-CAACTTTCAGTCC-AGGGTGTAG
------------------------------------------------------------
CGTGGTACCGGGCCGCGGGAGCGGACACTGGCAAAGCTTAACTTTCCG-CCTAGGGTGTAG

ACCCTTTACAGCCGCATTGCCACGGTGTAGACAC-CGGTGGACCCGCT-CTGGCTCAGAG
----------------------------------------------------------
AGTGTTTGCAGTCGTATTCCCGCGGTGTAGACACTC-GTGGGCACGCTCCT-GCTTGGTG
```

```
HAMSTER 33   AGATCAGAAATGTTCCAGAGGT-GGGATGGGGCCAGA-GTGCCTGCCCCTTGAACC-GTC
             |||  ||||| ||||||||||| ||||  |||| |||  |||||||||||  |||  |||
MOUSE   1    AGACCAGAATTGTTCAGAGAGTCGGGG-TGGGG-CTGAGGTGCCTGCCCCTTG-ACCAGTC

CCAGGGAC-CAGAGGTGACAAAGTGGCAACACAGGTCCTGCCTGGGAATCTGGTCTGCTC
             |||  ||| |||||||||||||||||||||||||||||||||||||||||||||||||||
             CCA-GGACTGAGAGGTGACAAAGTGGCAACACAGGTCCTGCCTGGGAATCTGGTCTGCTC

CTA-CTTAGTAAAGCTGCCTGGTGTCACACAAGAGGCCCCCACTT-ATTCCTGCACCCCT
             ||| ||||||||||||||||||||||||  ||||||||||| |||| |||||||||||||
             -TAACCTAGTAAAGCTGTCTGGTGTCACCCAAGAGGCTCCCTCCACAT-CCTGCACCCCT

GGTGG-TAGGTGGCCGTCTT-CTCCCCCTGCAGCC-ACCAGGCTCC-CCTGAGAACACTGCC
             |||||  |||  ||| |||| ||||  ||||||||| |||||||| |||||||||| |||
             GATGGCT-GATGGCATCTTTCTCCCCTTGCACCCCAGGGTTCTCCTGGGAATACT-CT

GG-CAGTCCTCATTGACAGGCAGTATTCGCTCTGCCCCCACCCTGTGAATTGCAGG
             || |||||||  ||||||||||||  |||||  ||| |||||||||||| ||||||
             GGGCTCTCCTTATTGACAGGCAGCAGCATTTGCCCTGCCCCACCTGTGACTGCAGG

GCTGGCAGGTCCTCAGGCAGCTGGCAAACCGCTGGCAACTGAGAGATACAGGGCCAGG
             |||||||||||||||||||||||||||||||| |||||||||||||| |||||||||
             ACTGGCAGGTCCTTGGGCAGCTGGCAAACTGCCTGAGCAACTGAGAAATACAAGGCCAGG

GCCAGGGCAGTCCCGTCCCCGGAGGCAGGAGGGGACGTGC-TGGGAAAGTTCTCTCTC
             ||||||||||||||  ||||||||||||||||  ||||| ||||||||||||||||
             GCCAGGGCAGTCCTGTCCCCGGAGGCAGGAGGAGGAGAC-TGCCTGGGAAAGTTCTCTC

TCAGGCCCCAGGTTGGTGACTGCAGAAGGCTTCTGTCAAATCTCTTTT 487
             |||  |||  |   ||||||||||||||| |||||||||| ||||||
             --AGG-----G-TTGGTGACTGCAGAAGACTTTGTCAAATTTTTTT 449
```

*FIG. 2A*

```
HAMSTER 996  TGAGCACGC-TGCCCCTCCCAGAGTCCCCACAGCCT-CCAGATGGACTAGAACACAGTTC
             ||||||| | |||||||||||||||||||||||||| |||||||||||||||||| |||
MOUSE   921  TGAGCA-GCTTGTCACTCCCAGAATCCCCAC-GGCTGGCAGATGGACTAGTGCACAACTC

GGCTGTGGCTGCACATAACT-AACAGAGGATAGATGGTGGGTCCCAGCCCAAC-AGTGCC
             |||||||||||||||||| | ||||||||||||| ||||||||| |||||||| |||||
             AGCTGTGGCTGCACATAA-TAAATAGAGGATAGATGGTGGGCCCCAGCCCAGCGA-TGTC

TGGCAATCACCCAGAGCCACCAGCTAACGGCCTTGGCTTAGTTTTTTGCCTGGGTGTGAT
             ||||| ||||| |||||| ||||||||||||||||||| |||||  ||||||||||||
             TGGCAGTCACCCAGAGACACTAGCTAACGGCCCAGGCTTAG--TCTTGCCTGGGTGTGAT

CAGGCAGCCCTCCAAAACTGCCCGGACTCCATGACAAGTTTTGCTTGTTCTATAGAGCAC
             ||||||||| ||||||  || |||| |||||||| ||||| |||||||||| ||||||
             CAGGCAGTTCTCCAAAAGTG-CCTGACTCCATGAGAATCTTGGAGGCATCTTCTATTGAGCAC

AGTTCCTTTCTAGGTCTCTGGGGCAAGGGACATCGGGAGACATCTTCCTGCAACAGCTCCAG
             |||||||||||| ||||| |||||||||  |||||||||||||||||||||||||| ||||
             AGTTCCTTTCTAGATCCGGGGCAGGGGATATCTGGAGGCATCTTCTTGCAACACCTCCAG

TCACTGGACCAC-CAGGCTCGCGCCTGT-CTTTGG-T-GTG-TGGCCCTGAGTCTCCTAAG
             | | |||||||| ||||| | |||| | |||| | | |||   ||||||||||| | |||
             TTATTGGACCACTGGGGCTCGCCCCTATGCTTGGGATAG-GATGGCCTTGAGTCT-CTAAG

TGGCCCAA-A-CCTGTGAAGACCCCTCCAACCACAGTTTTGCTTCTAAATTGTACCCCAA
             ||  |||| | ||  | ||| ||  | ||||||||||| ||||||  ||  || ||||||
             AGG-TCAAGATCC-ATGAAAACCTCTCCAACCAGAGTTCTGCTTCCAAGTTGAACCCCAA
```

FIG. 2B

```
CACACCTAGCAAAATT-GAAACCCCACCAGAA----G-TCCCCCAGATCTGGCTTTCCGGCT
|||||||||||||||| |||||||||||||||    | |||||||||||||||||||||||
CACACCTAGCAAATTAG-AACCACAGCAGAAGGGGCCCCCCCGGATCTGGCTTTCCGGCT

A-T--T-GC---TG----GCAAGGGGGAGTGACTCCCGGCCCATTCAATCCAGGCCCCGCG
  |  | ||   ||    ||||||||| ||||||||| ||||||||||||||||||||||
ATTGCTAGCAATTGCTAGCAAGGGGGAGTGACTCTCTGTCCATTCAATCCAGGCCCCGCG

TGTTCCTCAAACAAGAAGCCACGTAAACATAAACCGAGCCTCCATGCTGACCCTTGCCCA
|||||||||||| ||||||||||| |||||| |||||||||||| |||||||||||| |
TGTCCCTCAAACAAGAGGCCACACACAAATAGGTCCGGGCCTCGATGCTGACCCTCATCCA

-TCGAGGTACTCAATGTTCACGTGATATCCACACCCAGAGGGTCCTGGGGTGGGTGCATG
 |||||||| |||||||||||||||||||||||||||||||||||||||||| ||||||
CT-TAAGTGCTCGATATCCACGTGACATCCACACCCAGAGGGTCCTGGGGTGGTTGGGTG

AGCCCCAGAATGCAGG-CTTGATAACCGAGACCCTGAATCGGGCAGTGTCCACAAGGGCG
|||| ||||||||||| ||| ||||||||||| |||||||| |||||||||||||||||
ACCCCCAGAATGCAGGCCTAG-TAACCGAGACATTGAATGGGGCAGTGTCCACAAGGGCG

GAGGCCCAGTCATG--CATGTTCGGGCCTATGGGGCCAGCACCCAAACGCCAAAACTCTCC
|||| ||||| |||  |||||||||||| ||  ||||| |||||||| |||||||||| |
GAGG-CTATTCCTGTACAT-CT-GGGCCTACGGAGCCAGCACCCATCGCCAAAACTCTTC

ATCCTCTTCCTCAATCTCGGCTTTCTCTCT--C-TCTCTCTTTTT-TT-TT-TTTATTT
|||| ||||||||||| || ||||||||||| | ||||||||||| || || ||| ||
ATCCTCTTCCTCAATCTC-GCTTTCTCTCTCGCTTTTTTTTTTTCTTCTTCTTTTT

TTTTTTTTGCAAAAGGAGGGGAGAGGGTAAAAAAATGCTGCACTGTGCGGCTAGGCC
|||||||| |||| |||||||||||||||||||||||||||||||||||| |||||
TTTTTTTTCAAAAAGGAGGGGAGAGGGTAAAAAAATGCTGCACTGTGCGGCGAGGCC
```

```
HAMSTER  1775      TCTCTCTCTTTTTTTTATTTTTTTTGCAAAAGGAGGGAGAGGGGTAAAA
                   ||||||||||||||||| ||||||||||||||||||||||||||||||
HAMSTER GENE 1     TCTCTCTTTTTTTTTTT-TTTTTTTTTTTCCAAAAGGAGGGAGAGGGGTAAAA

AAATGCTGCACTGTGCGGCTAGGCCGGTGAGTGAGCGGCCGGAGCCAATCAGCGCTCGC
                   |||||||||||||||||||||||||||||||||||||||||||||||||||||||||||
                   AAATGCTGCACTGTGCGGCTAGGCCGGTGAGTGAGCGGCCGGAGCCAATCAGCGCTCGC

CGTTCCGAAAGTTGCCTTTTATGGCTCGAGTGGCCGCTGTGGGCGTCCTATAAAACCCGGC
                   ||||||||||||||||||||||||||||||||||||||||||||||||||||||||||||
                   CGTTCCGAAAGTTGCCTTTTATGGCTCGAGTGGCCGCTGTGGGCGTCCTATAAAACCCGGC

GGCGCAACGCGCAGCCACTGTCGAGTCCGCGTCCACCCGCGAGCACAGGCCTTTCGCAGC
                   ||||||||||||||||||||||||||||||||||||||||||||||||||||||||||||
                   GGCGCAACGCGCAGCCACTGTCGAGTCCGCGTCCACCCGCGAGCACAGGCCTTTCGCAGC

TCTTTCTTCGCCGCTCCACACACCCGCCACCAGGTAAGCAGGACAGGGACAACAGGCCCAGCCGGCC
                   ||||||||||||||||||||||||||||||||||||||||||||||||||||||||||||
                   TCTTTCTTCGCCGCTCCACACACCCGCCACCAGGTAAGCAGGACAGGGACAACAGGCCCAGCCGGCC

ACAGCCCTCCCGTGGGCAGTGACCGCGCTGACCCGCTGCAGGGTCGCGGGGACACTCGGCGCGGACA
                   ||||||||||||||||||||||||||||||||||||||||||||||||||||||||||||
                   ACAGCCCTCCCGTGGGCAGTGACCGCGCTGACCCGCTGCAGGGTCGCGGGGACACTCGGCGCGGACA

CCGGGGAAGGCTGGAGGTGTGTGCCGGCGGTGCCGCGGAGCGGAGACACTTTCAGATCCAACTTTC
                   ||||||||||||||||||||||||||||||||||||||||||||||||||||||||||||
                   CCGGGGAAGGCTGGAGGTGTGTGCCGGCGGTGCCGCGGAGCGGAGACACTTTCAGATCCAACTTTC

AGTCCAGGGTGTAGACCCTTTACAGCCGCATTGCCACGGTGTAGACACCGGTGGACCCGC
                   ||||||||||||||||||||||||||||||||||||||||||||||||||||||||||||
                   AGTCCAGGGTGTAGACCCTTTACAGCCGCATTGCCACGGTGTAGACACCGGTGGACCCGC
```

FIG. 3A

```
TCTGGCTCAGAGCACGCGGCTTGGGGAACCCATTAGGGTCGCAGTGTGGGCGCTATGAG
TCTGGCTCAGAGCACGCGGCTTGGGGAACCCATTAGGGTCGCAGTGTGGGCGCTATGAG

AGCCGATGCAGCTTTCGGGTGTTGAACCGTATCTGCCCACCTTGGGGGAGGACACAAGG
AGCCGATGCAGCTTTCGGGTGTTGAACCGTATCTGCCCACCTTGGGGGAGGACACAAGG

TCGGGAGCCAAACGCCACGATCATGCCTTGGTGGCCCATGGGTCTCTTTGTCTAAACCGGTT
TCGGGAGCCAAACGCCACGATCATGCCTTGGTGGCCCATGGGTCTCTTTGTCTAAACCGGTT

TGCCCATTTGGCTTGCCCGGCGGGGCGCGGCCCCGGCTCGGCCCCGGGTGGGGCT
TGCCCATTTGGCTTGCCCGGCGGGGCGCGGCCCCGGCTCGGCCCCGGGTGGGGCT

GGGTTGCCACTGCGCTTGCCGCGCGCGCTCTATGGCTGGTGGCGCGTGCACGCTGGGGA
GGGTTGCCACTGCGCTTGCCGCGCGCGCTCTATGGCTGGTGGCGCGTGCACGCTGGGGA

GGGAGCCCCTTCCCTCTTCCCCCTCTCCCCAAGTTAAACTTGCCGCTGCCGTATTGAGACTTGG
GGGAGCCCCTTCCCTCTTCCCCCTCTCCCCAAGTTAAACTTGCCGCTGCCGTATTGAGACTTGG

AGCGCGGCCACCGGGTTGGGCGAGGGGCGGGGCCCGTTGTCCGAAGGGCGGGGTCGCAG
AGCGCGGCCACCGGGTTGGGCGAGGGGCGGGGCCCGTTGTCCGAAGGGCGGGGTCGCAG
```

*FIG. 3B*

```
CGGCTTCGGGGCGCCTGCTCGGCGCTTCCTGCTGTGGTGCCTCCCGCGCGCACT   ||||  ||||||||||||||||||||||||||||||||||||||||||||||||   AGGATTCGGGGCGCCTGCTCGCGCTTCCTGCGTGTGGTGCCTCCCGCGCGCACT

AG-CCGCCCGCCGGGGCGGGGCGAAGGCGGGGCCTTGCGCCCGTTTGGGGAGGGGCGGAGGC   || ||||||||||||||||||||||||||||||||||||||||||||||||||||||||   AGACCGCCCGCCGGGGCGGGGCGAAGGCGGGGTCTTGCGCCCGTTTGGGGAGGGGCGGAGAC

CTGGCCTTCCTGCCGTGGGCCCGCCTCCGGACCAGCGTTTGCCTCTTATGGTAATAACGCG   ||||||||||||||||||||||||||||||||||||||||||||||||||||||||||||   CTGGCCTTCCTGCCGTGGGCCCGCCTCCGGACCAGCGTTTGCCTCTTATGGTAATAACGCG

GCCGGCCTGGGCTTCCTTTGTCCCCTGAGTTTGGGCGCGCCCCCTGGCGGCCCGAGGC   ||||||||||||||||||||| ||||||||||||||||||||||||||||||||||   GCCGGCCTGGGCTTCATTTGTCCCCTGAGTTTGGGCGCGCCCCCTGGCGGCCCGAGAC

CGCGGCTTGCCGGAAGTGGGCAGGGCGGCAGGGCTGCGCCTAGTGGCCCGCTAGTGACC   ||||||||||||||||||||||||||||| ||||||||||||||||||||||||||||   CGCGGCTTGCCGGAAGTGGGCAGGGCGGCAACGGCTGCGCCTAGTGGCCCGCCAGTGACC

GCGACCCCTCTTTTGTGCCCTGATATAGTTCGCC 3006   |||||||||||||  ||||||||||||||||||   GCGACCCCTCTTTTTGCCCTGATATAGTTCGCC 1232
```

*FIG. 3C*

β-ACTIN AND RPS21 PROMOTERS AND USES THEREOF

This application claims the benefit of priority of U.S. Provisional Patent Application No. 60/480,768, filed Jun. 24, 2003, the entire contents of which are incorporated by reference.

FIELD OF THE INVENTION

This invention relates to regulatory gene elements such as promoters and uses thereof, for example, for expression of proteins. More specifically, this invention relates to β-actin and ribosomal protein S21 gene promoters.

BACKGROUND OF THE INVENTION

Every eukaryotic gene contains regulatory elements driving transcription of that gene. Such regulatory elements include promoters, which are typically positioned immediately upstream of the coding sequence in a gene. Promoters regulate transcription by providing binding sites for transcription factors, which are a part of the transcription machinery. Promoters are commonly used to express proteins in cell culture and in vivo. Many promoters are known and used for expression of proteins in various expression systems. Examples of promoters include cytomegalovirus (CMV) immediate early promoter, Rous sarcoma virus genome large genome long terminal repeats (RSV), Simian Virus 40 (SV40) promoter, interferon gene promoter, metallothionein promoter, and the thymidine kinase promoter and others, e.g., as described in Fernandez et al: (1999) Gene Expression Systems, Academic Press. However, there is still a need in the art to provide promoters that are capable of generating high levels of expression and/or sustain expression for an extended period of time.

β-actin is a structural protein and is usually expressed in all species, from protozoa to eukaryotes, including humans. The human and chicken β-actin promoters have been previously described. The β-actin promoter, in general, shows a more ubiquitous activity than the CMV promoter which is widely used (Xu et al. (2001) Gene 272:149-156). The chicken β-actin promoter was shown to exhibit a higher activity than viral CMV and SV40 promoters but only when it is linked to a CMV enhancer sequence (Xu et al., supra).

The ribosomal protein S21 (rpS21) which is associated with the 40S subunit of the ribosome. The promoter of the human rpS21 gene was previously identified (GenBank® accession No. AJ250907). Similarly to most ribosomal gene promoters, it lacks conventional transcription elements such as the TATA box and CAAT sequence (Smirnova et al. (2000) Bioorg. Khim. 26(5):392-396).

SUMMARY OF THE INVENTION

This invention provides novel β-actin promoters that have a low level of sequence homology to previously known β-actin promoters (such as, e.g., human and chicken). This invention further provides novel rpS21 promoters that have a low level of sequence homology to previously known rpS21 promoters (such as, e.g., human and mouse).

The present invention is based, in part, on the discovery and isolation of β-actin and rpS21 promoters from a Chinese hamster ovary (CHO) cell line. This invention is further based, in part, on an observation that the hamster β-actin promoter has a significantly higher activity than the CMV promoter. The invention is further based, in part, on an observation that the rpS21 promoter is at least as active as the hamster β-actin promoter when used for expressing certain genes. The invention provides nucleotide sequences for these promoters and includes variants of the nucleotide sequences having promoter activity. In some embodiments, a β-actin promoter of the invention is derived from a rodent, for example, hamster, rat, and mouse. The rpS21 promoter is typically derived from a hamster.

The invention further provides vectors comprising a β-actin or a rpS21 promoter of the invention operably linked to a heterologous nucleic acid. In certain embodiments, a vector of the invention comprises a promoter that is operably linked to a heterologous nucleic acid which encodes a heterologous expression product such as, e.g., a therapeutic protein or a fragment thereof. In illustrative embodiments, the expression product is acid sphinogomyelinase (ASM), α-glucosidase (GAA), or tissue plasminogen activator (tPA).

The invention also provides host cells transfected with a vector of the invention. In illustrative embodiments, the host cell is a mammalian cell such as, e.g., CHO, HEK, and BHK.

Methods for producing a protein are also provided. Methods for producing a protein include, for example, culturing a cell transfected with a vector comprising a β-actin promoter and/or a rpS21 promoter of the invention operably linked to a heterologous nucleic acid encoding a protein, and recovering the protein. In some embodiments, the heterologous expression product is a secretory protein, which is recovered from the medium. In illustrative embodiments, the protein is ASM, GAA, or tPA.

BRIEF DESCRIPTION OF THE FIGURES

FIG. 1A shows an alignment between portions of nucleotide sequences of a hamster β-actin promoter (SEQ ID NO:1) and a rat β-actin promoter (SEQ ID NO:2), demonstrating a 79% identity between nucleotide (nt) 487 to nt 893 of SEQ ID NO:1 and nt 1 to nt 417 of SEQ ID NO:2. The rat β-actin promoter (SEQ ID NO:2) has a 67% identity over the entire length of hamster β-actin promoter (SEQ ID NO:1).

FIGS. 1B, 1C, 1D, 1E, and 1F show an alignment between portions of nucleotide sequences of a hamster β-actin promoter (SEQ ID NO:1) and a rat β-actin promoter (SEQ ID NO:2), demonstrating an 83% identity between nt 1047 to nt 3006 of SEQ ID NO:1 and nt 546 to nt 2493 of SEQ ID NO:2.

FIG. 2A shows an alignment between portions of nucleotide sequences of a hamster β-actin promoter (SEQ ID NO:1) and a mouse β-actin promoter (SEQ ID NO:3), demonstrating an 84% identity between nt 33 to nt 487 of SEQ ID NO:1 and nt 1 to nt 449 of SEQ ID NO:3. The mouse β-actin promoter sequence (SEQ ID NO:3) has an 80% identity over the entire length of hamster β-actin promoter sequence of SEQ ID NO:1.

FIGS. 2B, 2C, 2D, 2E, and 2F show an alignment between portions of nucleotide sequences of a hamster β-actin promoter (SEQ ID NO:1) and a mouse β-actin promoter (SEQ ID NO:3), demonstrating an 83% identity between nt 996 to nt 3006 of SEQ ID NO:1 and nt 921 to nt 2953 of SEQ ID NO:1.

FIGS. 3A, 3B, and 3C show an alignment between portions of nucleotide sequences of a hamster β-actin promoter (SEQ ID NO:1) and a hamster β-actin gene (Genbank® Accession No. U20114; SEQ ID NO:4), demonstrating a 98% identity between nt 1775 to nt 3006 of SEQ ID NO:1 and nt 1 to nt 1232 of SEQ ID NO:4. The hamster β-actin gene sequence has a 40% identity over the entire length of the hamster β-actin promoter sequence of SEQ ID NO:1.

FIG. 4 shows an alignment between portions of nucleotide sequences of hamster β-actin promoter (SEQ ID NO:1) and a previously known human β-actin promoter (GenBank® Accession No. gi28337; SEQ ID NO:5), demonstrating a 94% identity between nt 113 to nt 148 of SEQ ID NO:1 and nt 38 to nt 73 of SEQ ID NO:5, an 83% identity between nt 362 to nt 433 of SEQ ID NO:1 and nt 303 to nt 374 of SEQ ID NO:5, a 90% identity between nt 1728 to nt 1764 of SEQ ID NO:1 and nt 1791 and nt 1830 of SEQ ID NO:5, and a 91% identity between nt 1797 to nt 1966 of SEQ ID NO:1 and nt 1840 to nt 2007 of SEQ ID NO:5. The human β-actin promoter sequence (SEQ ID NO:5) shows a 10% identity over the entire length of the hamster β-actin promoter sequence of SEQ ID NO:1.

FIG. 5 shows an alignment between portions of nucleotide sequences of hamster β-actin promoter (SEQ ID NO:1) and a previously known chicken β-actin promoter (GenBank® Accession No. gi2170437; SEQ ID NO:6), demonstrating an 83% identity between nt 1878 to nt 1919 of SEQ ID NO:1 and nt 186 to nt 227 of SEQ ID NO:6. The chicken β-actin promoter sequence (SEQ ID NO:6) shows a 1% identity over the entire length of the hamster β-actin promoter sequence of SEQ ID NO:1.

FIG. 6A depicts a Northern blot for galectin, ferritin, and β-actin in CHO-K1 cells. Representative mRNAs were isolated from cells at 0, 4, 8, 10, and 15 hours following treatment of cells with actinomycin D.

FIG. 6B depicts relative mRNA expression levels for galectin, ferritin, and β-actin genes. Representative mRNAs were isolated from cells at 0, 4, 8, 10, and 15 hours following treatment of CHO-K1 cells with actinomycin D.

FIG. 7A depicts relative promoter strengths as measured in transient transfection assays in CHO-K1 cells for the following promoters: CMV, human EF-1, hamster GAPDH, hamster rpS21 and hamster β-actin. The representative promoters were cloned upstream of a red fluorescent protein (RFP) gene in the pDsRED-1 plasmid. The mean fluorescence was measured by FACS.

FIG. 7B depicts relative promoter strengths as measured in stable transfection assays in CHO-K1 cells for the following promoters: CMV, human EF-1, hamster GAPDH, hamster rpS21, and hamster β-actin. The representative promoters were cloned upstream of a red fluorescent protein (RFP) gene in the pDsRED-1 plasmid. The mean fluorescence was measured by FACS.

FIG. 8A depicts the expression of acid sphingomyelinase (ASM) protein in media from three pools of CHO-DXB11 cells transfected with a vector containing the ASM cDNA operably linked to either the CMV promoter or the hamster β-actin promoter. The expression of ASM was assessed in an enzymatic activity assay for ASM.

FIG. 8B depicts the expression of α-glucosidase (GAA) protein in media from three pools of CHO-DXB11 cells transfected with a vector containing the GAA cDNA operably linked to either the CMV promoter or the hamster β-actin promoter. The expression of GAA was assessed in an enzyme activity assay for GAA.

FIG. 9 depicts the expression of tPA protein in media from pools of CHO-DXB11 cells transfected with a vector containing the tPA cDNA operably linked to the hamster β-actin promoter. The expression of tPA was assessed using ELISA.

DETAILED DESCRIPTION OF THE INVENTION

In order that the present invention be more readily understood, certain terms are first defined. Additional definitions are set forth throughout the detailed description.

The term "promoter" refers to a regulatory element that directs the transcription of a nucleic acid to which it is operably linked. A promoter can regulate both rate and efficiency of transcription of an operably linked nucleic acid. A promoter may also be operably linked to other regulatory elements which enhance ("enhancers") or repress ("repressors") promoter-dependent transcription of a nucleic acid. The term "operably linked" refers to a nucleic acid placed in a functional relationship with another nucleic acid. A promoter is usually positioned 5' (i.e., upstream) of a transcription initiation site in the nucleic acid. A promoter, however, may include sequences 3' (i.e., downstream) of the transcription initiation site. A promoter may also encompass regions both 5' and 3' of the transcription initiation site of the operably linked nucleic acid.

The term "promoter activity" refers to the ability of a promoter to initiate transcription of a nucleic acid to which it is operably linked. Promoter activity can be measured using procedures known in the art or as described in the Examples. For example, promoter activity can be measured as an amount of mRNA transcribed by using, for example, Northern blotting or polymerase chain reaction (PCR). Alternatively, promoter activity can be measured as an amount of translated protein product, for example, by Western blotting, ELISA, calorimetric assays such as, e.g., Bradford assay (Bradford (1976) Anal. Biochem., 72:248), and various activity assays, including reporter gene assays and other procedures known in the art or as described in the Examples.

The term "vector" refers to viral or non-viral, prokaryotic or eukaryotic, deoxyribonucleic acid, ribonucleic acid or a nucleic acid analog, that is capable of carrying another nucleic acid. A vector may either carry a nucleic acid into a cell, referred to as "host cell," so that all or a part of the nucleic acid is transcribed or expressed. Alternatively, a vector may be used in an in vitro transcription assay. Vectors are frequently assembled as composites of elements derived from different viral, bacterial, or mammalian genes. Vectors contain various coding and non-coding sequences including sequences coding for selectable markers (e.g., an antibiotic resistance gene), sequences that facilitate their propagation in bacteria, or one or more transcription units that are expressed only in certain cell types. For example, mammalian expression vectors often contain both prokaryotic sequences that facilitate the propagation of the vector in bacteria and one or more eukaryotic transcription units that are expressed only in eukaryotic cells. It will be appreciated by those skilled in the art that the design of the expression vector can depend on such factors as the choice of the host cell to be transformed, the level of expression of protein desired, etc.

Vectors include, for example, plasmids, phagemids, and viral vectors. Vectors that have an existing promoter can be modified by standard recombinant DNA techniques known in the art to replace the promoter with any of promoter sequences set forth in SEQ ID NOs:1, 2, 3, or 39 or a variant thereof. In general, suitable vectors can either be chosen from those that are commercially available or they can be constructed using standard recombinant DNA techniques known in the art. (See, e.g., Molecular Cloning: A Laboratory Manual: 2nd edition, Sambrook et al., 1989, Cold Spring Harbor Laboratory Press.)

The terms "transformation" and "transfection" refer to intracellular introduction of a nucleic acid. A nucleic acid can be introduced into a plant or an animal cell or a prokaryotic or eukaryotic cell by a number of methods known in the art or described herein.

The term "isolated" refers to a deoxyribonucleic acid, a ribonucleic acid, or a nucleic acid analog having a polynucleotide sequence that is separated from other nucleic acid sequences in such a way that does not naturally occur. An isolated nucleic acid encompasses nucleic acids that may be partially or wholly chemically or recombinantly synthesized and/or purified by standard techniques known in the art.

The term "variant" in reference to a promoter sequence refers to a nucleotide sequence that is substantially identical over the entire length to the promoter sequence or to its complementary strand over the entire length thereof, provided that the variant has promoter activity.

Variants of β-actin promoters may be the same length as the nucleotide sequences of SEQ ID NOs:1, 2, or 3, or shorter, so long as they are at least 1250 nucleotides in length. Variants of rpS21 promoters may be the same length as the nucleotide sequence of SEQ ID NO:39, or shorter, so long as they have promoter activity. Variants of the β-actin promoter can be naturally occurring, for example, naturally occurring β-actin promoters isolated from species other than human and chicken, or they can be generated artificially. The identity between the hamster β-actin promoter set forth in SEQ ID NO:1 and a variant thereof, when optimally aligned, is at least 45%, 50%, 55%, 60%, 65%, 70%, 75%, 80%, 85%, 90%, 92%, 93%, 94%, 95%, 96%, 97%, 98%, or 99% over the entire sequence of SEQ ID NO:1 from nt 1 to nt 3007. Similarly, the identity between the rat β-actin promoter set forth in SEQ ID NO:2 and a variant thereof is at least 60%, 65%, 70%, 75%, 80%, 85%, 90%, 92%, 93%, 94%, 95%, 96%, 97%, 98%, or 99% over the entire sequence of SEQ ID NO:2 from nt 1 to nt 2493. The identity between the mouse β-actin promoter of SEQ ID NO:3 and a variant thereof is at least 55%, 60%, 65%, 70%, 75%, 80%, 85%, 90%, 92%, 93%, 94%, 95%, 96%, 97%, 98%, or 99% over the entire length of SEQ ID NO:3 from nt 1 to nt 2953. Similarly, identity between the hamster rpS21 promoter set forth in SEQ ID NO:39 and a variant thereof, when optimally aligned, can be at least 40%, 50%, 55%, 60%, 65%, 70%, 80%, 90%, 91%, 92%, 93%, 94%, 95%, 96%, 97%, 98%, or 99% over the entire length of SEQ ID NO:39 from nt 1 to nt 1958.

Variants of β-actin promoters may, for example, include orthologs of the β-actin promoters in other species, including rodents and other mammals, but excluding human and chicken β-actin promoters and known variants thereof. Variants of the promoters of the invention may also be found in other rodent species such as, for example, guinea pig, woodchuck, muskrat, gerbil, squirrel, chipmunk, prairie dog, beaver, porcupine, and vole.

The term "variants" further encompasses fragments of any one or more of promoters of the invention that have promoter activity. Variants of the β-actin promoters are at least 1250 nucleotides in length. Variants of the β-actin promoters of the invention can be derived, for example, by 5' truncations of the hamster β-actin promoter set forth in SEQ ID NO:1. In some embodiments, β-actin promoter variants include sequences from nt 50 to nt 3000, from nt 100 to nt 3000, from nt 150 to nt 3000, from nt 200 to nt 3000, from nt 250 to nt 3000, from nt 500 to nt 3000, from nt 1000 to nt 3000, or from nt 1500 to nt 3000 of SEQ ID NO:1. In other embodiments, β-actin promoter variants may be derived by 5' truncations of the sequence set forth in SEQ ID NO:2 and include, for example, from nt 50 to nt 2490, from nt 100 to nt 2490, from nt 150 to nt 2490, from nt 200 to nt 2490, from nt 250 to nt 2490, from nt 500 to nt 2490, or from nt 1000 to nt 2490 of SEQ ID NO:2. β-actin promoter variants may also be derived by 5' truncations of the sequence set forth in SEQ ID NO:3 and include, for example, from nt 50 to nt 2950, from nt 100 to nt 2950, from nt 150 to nt 2950, from nt 200 to nt 2950, from nt 250 to nt 2950, from nt 500 to nt 2950, from nt 1000 to nt 2950, or from nt 1500 to nt 2950 of SEQ ID NO:3. Longer fragments of the hamster β-actin promoter can be derived, for example, by 5' truncations of the longer hamster promoter nucleotide sequence set forth in SEQ ID NO:7. Such variants include, for example, sequences from nt 50 to nt 3668, from nt 100 to nt 3668, from nt 150 to nt 3668, from nt 200 to nt 3668, from nt 250 to nt 3668, from nt 500 to nt 3668, or from nt 600 to nt 3668.

Variants of rpS21 promoters may be derived by 5' truncations and/or 3' truncations of the sequence set forth in SEQ ID NO:39. Such variants include, for example, sequences from nt 50 to nt 1958, from nt 100 to nt 1958, from nt 150 to nt 1958, from nt 200 to nt 1958, from nt 250 to nt 1958, from nt 500 to nt 1958, from nt 1000 to nt 1958, from nt 1 to nt 1900, from nt 1 to nt 1850, from nt 1 to nt 1800, from nt 1 to nt 1750, from nt 1 to nt 1700, from nt 1 to nt 1600, or from nt 1 to nt 1500.

In certain embodiments, a β-actin promoter of the invention comprises a contiguous stretch of at least 1250, 1500, 1550, 1600, 1650, 1700, 1750, 1800, 1850, 1900, 1950, 2000, 2500, or 3000 nucleotides from SEQ ID NOs:1, 2, or 3. Such contiguous stretches of SEQ ID NOs:1, 2, and 3 may also contain a mutation (insertion or deletion) so long as the mutant sequence retains at least some functionality of the original sequence and the capacity to hybridize to the respective sequences of SEQ ID NOs:1, 2, or 3 under low, medium or high stringency conditions. A contiguous stretch of a β-actin promoter can be derived by 5' truncations of any of sequences set forth in SEQ ID NO:1, 2, 3, or 7 or variants thereof as described above.

In other embodiments, a rpS21 promoter of the invention comprises a contiguous stretch of at least 500, 600, 700, 800, 900, 1000, 1100, 1200, 1300, 1400, 1500, 1600, 1700, 1800, 1850, or 1900 nucleotides from SEQ ID NO:39.

β-actin promoter variants of the invention further include nucleotide sequences that hybridize to the entire length of the β-actin promoter sequences shown in SEQ ID NOs:1, 2, or 3, or their complements and that have at most 0, 1, 2, 3, 4, 5, 10, 15, 20, 25, 30, 35, 40, 45% base pair mismatches. rpS21 promoter variants of the invention include nucleotide sequences that hybridize to the entire length of the rpS21 promoter sequence shown in SEQ ID NO:39, or its complement, and that have at most 0, 1, 2, 3, 4, 5, 10, 15, 20, 30, 40, 45, 50, 55, 60% base pair mismatches. The percentage of base pair mismatches can be determined by standard techniques known in the art or as described herein. The term "heterologous" when used in reference to a nucleic acid, means a nucleic acid other than the nucleic acid that a promoter is operably linked to in a naturally occurring genome. For example, the term "heterologous" refers to any nucleic acid other than the hamster β-actin gene when such a nucleic acid is operably linked to a hamster β-actin promoter. Likewise, the term "heterologous" refers to any nucleic acid other than the rat β-actin gene when such a nucleic acid is operably linked to a rat β-actin promoter. Similarly, the term "heterologous" refers to any nucleic acid when such a nucleic acid is operably linked to the mouse β-actin promoter. Analogously, this term also refers to any nucleic acid other than the hamster rpS21 gene when such a nucleic acid is operably linked to a hamster rpS21 promoter.

The term "transgenic" refers to any animal containing genetically manipulated cells in which a promoter of the invention is no longer operably linked to the same nucleic acid as in a naturally occurring genome. The term "transgenic" encompasses, for example, an animal containing cells with a promoter of the invention or a variant thereof integrated within the animal's chromosome. The term "transgenic" also encompasses an animal containing cells with an extrachromosomally replicating DNA sequence comprising a promoter of the invention or a variant thereof. The transgenic animal may be a mammal such as a rodent or human.

This invention is based, in part, on the discovery and isolation of novel promoters for the β-actin and rpS21 genes. Specifically, this invention features rodent β-actin promoters including, but not limited to, hamster, rat and mouse, and the hamster rpS21 promoter. This invention is based on the discovery and demonstration that β-actin promoters of the invention have promoter activity that is higher than the CMV promoter's activity, as described in the Examples. The invention is further based on the discovery that the hamster rpS21 promoter is at least as active as the hamster β-actin promoter when used for expressing certain genes.

The invention provides nucleotide sequences for rodent β-actin promoters, including hamster, rat, and mouse, and methods of use thereof. The invention further provides methods for identification and isolation of variants of promoters of the invention, including homologs and fragments of promoters that have promoter activity. Additionally, the invention provides a nucleotide sequence for the hamster rpS21 promoter, and methods of use thereof.

In the experiments leading to the present invention, a genomic clone for the hamster β-actin promoter was isolated from CHO cells following its identification as an active promoter by a technique called Serial Analysis of Gene Expression or "SAGE" (Valculesco et al. (1995) Science, 270:484-487 and Valculesco et al. (1987) Cell, 88:243-251). The SAGE technique can be used for transcription profiling of an entire genome. β-actin promoter was identified as one of the most active promoters in CHO cells using SAGE. This led to the cloning of the promoter for β-actin in CHO cells. A similar approach was used for the isolation of the hamster rpS21 promoter from CHO cells. This approach may be used for transcription profiling of other genomes to confirm that corresponding β-actin promoters or rpS21 promoter are active in another genome. Such a promoter can be cloned using standard techniques known in the art or those described here. Variants of promoters of the invention can be identified by hybridization to one or more of promoter sequences set forth in SEQ ID NOs:1, 2, 3, or 39. It is well known that the melting temperature (Tm) of a double-stranded nucleic acid decreases by 1-1.5° C. with every 1% decrease in homology (see, e.g., Bonner et al. (1973) J. Mol. Biol., 81:123). Species homologs, therefore, can be identified, for example, by hybridizing a putative nucleotide sequence with a nucleotide sequence of SEQ ID NOs:1, 2, 3, or 39, or a variant thereof, and comparing the melting temperature of such a hybrid with the melting temperature of a hybrid comprising a nucleotide sequence of SEQ ID NOs:1, 2, 3, or 39, or a variant thereof and a complementary nucleotide sequence. The number of base pair mismatches can then be calculated for the test hybrid. Therefore, a smaller difference between the melting temperatures of the test hybrid and a hybrid containing a putative homolog of any one of sequences in SEQ ID NOs:1, 2, 3, or 39, will indicate a greater homology between the putative nucleotide sequence and a promoter sequence of the invention. For example, variants in other rodent species such as guinea pig, woodchuck, muskrat, gerbil, squirrel, chipmunk, prairie dog, beaver, porcupine, and vole, may exhibit a greater homology to promoters of the invention and variants thereof.

A variety of factors are known to affect the efficiency of hybridization of two strands of nucleotide sequence. These may include, for example, length of nucleotide sequence, salt concentration and G/C content of the sequences. For example, for hybridization of long fragments of DNA, Howley et al. (1979) J. Biol. Chem., 254:4876, determined that the melting temperature at which 50% of a DNA is hybridized to a complementary strand is defined by:

$$T_m = 81.5 + 16.6 \log M + 41(\% \ G + \% \ C) - 500/L - 0.62F,$$

where
M is molar concentration of monovalent cations;
(% G+% C) is the respective fraction of G and C nucleotides in the sequences;
L is length of the hybrid DNA; and
F is molar concentration of formamide.

Appropriate hybridization conditions can be selected by those skilled in the art with minimal experimentation as exemplified in Ausubel et al. (1995) Current Protocols in Molecular Biology, John Wiley & Sons, sections 2, 4, and 6. Additionally, stringent conditions are described in Sambrook et al. (1989) Molecular Cloning: A Laboratory Manual, 2nd ed., Cold Spring Harbor Press, chapters 7, 9, and 11.

A non-limiting example of low stringency hybridization conditions is as follows. Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll™, 1% BSA, and 500 µg/ml denatured salmon sperm DNA. Hybridizations are carried out in the same solution with the following modifications: 0.02% PVP, 0.02% Ficoll™, 0.2% BSA, 100 µg/ml salmon sperm DNA, 10% (wt/vol) dextran sulfate, and 5-20×106 32P-labeled probe is used. Filters are incubated in hybridization mixture for 18-20 h at 40° C., and then washed for 1.5 hours at 55° C. in a solution containing 2×SSC, 25 mM Tris-HCl (pH 7.4), 5 mM EDTA, and 0.1% SDS. The wash solution is replaced with fresh solution and incubated for an additional 1.5 hours at 60° C. Filters are blotted dry and exposed for autoradiography. Other conditions of low stringency well known in the art may be used (e.g., as employed for cross species hybridizations).

A non-limiting example of high stringency hybridization conditions is as follows. Prehybridization of filters containing DNA is carried out for 8 h to overnight at 65° C. in buffer containing 6×SSC, 50 mM Tris-HCl (pH 7.5), 1 mM EDTA, 0.02% PVP, 0.02% Ficoll™, 0.02% BSA, and 500 µg/ml denatured salmon sperm DNA. Filters are hybridized for 48 hours at 65° C. in the prehybridization mixture containing 100 µg/ml denatured salmon sperm DNA and 5-20×10$^6$ cpm of $^{32}$P-labeled probe. Washing of filters is done at 37° C. for 1 hours in a solution containing 2×SSC, 0.01% PVP, 0.01% Ficoll™, and 0.01% BSA. This is followed by a wash in 0.1×SSC at 50° C. for 45 minutes.

A non-limiting example of hybridization conditions of moderate stringency includes prewashing filters in 5×SSC, 0.5% SDS, 1.0 mM EDTA, pH 8.0; hybridizing in 50% formamide, 6×SSC at 42° C.; and washing filters in 0.5×SSC, 0.1% SDS at 60° C.

Variants of the promoters of the invention can also be identified by percent identity between nucleotide sequences for putative variants and the sequences set forth in SEQ ID NOs:1, 2, 3, or 39, or their complementary strands. Percent identity may be determined, for example, by visual inspection or by using various computer programs known in the art or as described in the Examples. For example, percent identity of two nucleotide sequences can be determined by comparing sequence information using the GAP computer program described by Devereux et al. (1984) Nucl. Acids. Res., 12:387 and available from the University of Wisconsin Genetics Computer Group (UWGCG). Percent identity can also be determined by aligning two nucleotide sequences using the BLAST® program (www.ncbi.nlm.nih.gov/BLAST) as described by Tatusova et al. (1999) FEMS Microbiol. Lett., 174:247. For example, for nucleotide sequence alignments using the BLAST® program, the default settings are as follows: reward for match is 2, penalty for mismatch is −2, open gap and extension gap penalties are 5 and 2 respectively, gap×dropoff is 50, expect is 10, word size is 11, and filter is OFF.

Promoters of the invention identified by sequence identity include, for example, sequences set forth in SEQ ID NOs:2 and 3 for rat and mouse β-actin promoters, that show 67% and 80% identity, respectively, to nt 1 to nt 3007 of hamster β-actin promoter sequence set forth in SEQ ID NO:1. Additional variants can be readily identified using the various techniques described herein and those known in the art.

Percent identity between the hamster β-actin promoter (SEQ ID NO:1) and known β-actin promoters can be determined as described. For example, when SEQ ID NO:1 is compared to the human β-actin promoter (SEQ ID NO:5) using BLAST® sequence alignment with default parameters, it exhibits only about a 10% identity over the entire length of SEQ ID NO:1. Similarly, when SEQ ID NO:1 is compared to the chicken β-actin promoter (SEQ ID NO:6), it exhibits only about a 1% identity over the entire length of SEQ ID NO:1. Due to such low levels of homology, the human and the chicken β-actin promoters are not considered to be variants of the hamster β-actin promoter sequence of SEQ ID NO:1. Further, the 3' portion of SEQ ID NO:1 shows significant homology to the 5' portion of the hamster β-actin gene sequence (GenBank® Accession No. U20114; SEQ ID NO:4). In particular, the first 1232 nucleotides of SEQ ID NO:4 show a 98% identity with the 3' portion of SEQ ID NO:1, as depicted in FIG. 3. This identity is in the region of the first intron in the hamster β-actin gene. Overall, SEQ ID NO:4 shows only 40% identity over the entire length of SEQ ID NO:1. Furthermore, no promoter activity has been described for SEQ ID NO:4, or fragments thereof.

Using BLAST® sequence alignment with default parameters, no homology is detected between the previously known human rpS21 promoter (nt 1-2344 of GenBank® Accession No. AJ250907) and nt 1 to 1958 of hamster rpS21 promoter of SEQ ID NO:39. Very low level of homology is detected between hamster rpS21 promoter of SEQ ID NO:39 and mouse genomic DNA that spans the mouse rpS21 gene (GenBank® Accession No. NT_039212). There are two regions of homology in the mouse sequences. The first is from nt 1775 to nt 1945 of SEQ ID NO:39 (137 out of 172 nts match). The second is from nt 580 to nt 851 of SEQ ID NO:39 (208 out of 274 nts match). These two regions of homology are separated by 923 nts in the hamster sequence (SEQ ID NO:39) and by 1745 nts in the mouse genomic sequence (NT_039212).

Accordingly, in some embodiments, an isolated promoter or a variant thereof having promoter activity comprises the nucleotides sequence(s) as set out from nt 1775 to nt 1945 of SEQ ID NO:39 and/or from nt 580 to nt 851 of SEQ ID NO:39. Optionally, such a promoter or variant further comprises all or a portion of SEQ ID NO:39 as set out from nt 852 to nt 1774.

Nucleotide sequences set forth in SEQ ID NOs:1, 2, 3, or 39, or variants thereof, can be used as probes for screening genomic libraries for the isolation of genomic sequences that hybridize to one or more of sequences set forth in SEQ ID NOs:1, 2, 3, or 39, or variants thereof.

A promoter, according to the invention, or a variant thereof is operably linked to a heterologous nucleic acid, which it expresses. The promoter can be used either alone or in combination with other regulatory elements such as, for example, enhancers and repressors. Alternatively, such a promoter can be integrated into the genome of a host cell or animal, thereby to express an endogenous gene in the host. A promoter according to the invention can be used in a vector for expression of heterologous nucleic acids. In certain embodiments, the heterologous nucleic acid encodes a therapeutic protein. Examples of therapeutic proteins include, but are not limited to, α-glucosidase, acid sphingomyelinase, insulin, tissue plasminogen activator, thyrogen stimulating hormone, erythropoietin, glucocerebrosidase, α-galactosidase and various antibodies. Examples of antibodies include but are not limited to, antibodies that bind members of the TGF-β family such as, for example, TGF-β-1, 2, and 3.

This invention further provides vectors comprising a promoter of the invention or a variant thereof which has promoter activity. In some embodiments, vectors of the invention include a suitable restriction enzyme site downstream of the promoter for insertion of the heterologous nucleic acid. Such a restriction enzyme site may include a restriction site for a single restriction enzyme or it may include restriction sites for a variety of restriction enzymes in order to facilitate insertion of many different heterologous nucleic acids. A vector according to the invention may also contain a polyadenylation sequence downstream of the site for inserting a heterologous nucleic acid. Vectors comprising promoters of the invention may also contain prokaryotic DNA elements for bacterial replication and an antibiotic selection marker for growth and selection of the vector in bacterial cells and additional DNA elements that control processing of transcripts such, e.g., termination signals. Vectors may further contain DNA sequences to direct secretion of a protein outside host cells.

In certain embodiments, a vector containing a promoter sequence of the invention is a bicistronic vector. Bicistronic vectors are designed, such that two nucleic acids can be transcribed to yield a single transcript. Such a transcript usually contains a first portion which is translated into one protein and a second portion translated into a second protein. One protein can be a protein of interest such as, a therapeutic protein, and a second protein may be used as a selectable marker. Bicistronic vectors usually contain a promoter and an internal ribosome entry site or IRES positioned between two nucleic acids. This permits transcription of the two nucleic acids as a single bicistronic mRNA. In this manner, a vector can be constructed that includes a β-actin promoter of the invention or a variant thereof and an IRES between two heterologous nucleic acids. A bicistronic vector containing a β-actin promoter of the invention or a variant thereof can be used for expressing a therapeutic protein such as, for example, acid sphinglomyelinase or α-glucosidase, in conjunction with a reporter gene.

The invention further provides assays for identification of those variants of β-actin and rpS21 promoters of the invention that have promoter activity. For example, a promoter of the invention or variant thereof is inserted in a suitable vector upstream of a reporter gene and the expression of the reporter gene is used as a determinant of promoter activity. For example, for identification of variants of promoters of the invention that have promoter activity, such a variant is cloned upstream of a reporter gene. A reporter gene may encode an enzyme which catalyzes a reaction which produces a visually detectable signal. Examples of such reporter genes include β-galactosidase and luciferase. Examples of other reporter genes include alkaline phosphatase, nopaline synthase, octopine synthase, β-glucoronidase, chloremphenicol acetyltransferase. In the Examples set forth below, a reporter gene encoding a Discosoma striata red fluorescent protein (RFP) is used for measuring promoter activity. Those skilled in the art, however, can use any suitable reporter gene and assay technique to determine promoter activity. Expression of a reporter gene from the promoter may be assayed in an in vitro expression system or it may be intracellular (e.g., in vivo).

The invention further provides host cells that have been transfected with a vector of the invention comprising a promoter operably linked to a heterologous gene. Such a host cell can be a prokaryotic cell or a eukaryotic cell. Host cells can either be cells in culture or be present in an animal. Examples of host cells in culture include, but are not limited to, HeLa cells, CHO cells, NS0, HEK cells, BHK cells, NIH-3T3, MDCK cells, and COS cells. Host cells in culture can be grown either in suspension or on microcarriers, as described in the Examples.

Many suitable methods can be used for introducing nucleic acids of the invention into a host cell. Vectors comprising promoter sequences of the invention can be introduced into either prokaryotic or eukaryotic cells. Examples of techniques that may be used for introduction of nucleic acids into eukaryotic cells include, for example, calcium phosphate precipitation, DEAE-Dextran transfection, electroporation, liposome-mediated transfection, transduction using viral vectors, etc.

Many suitable expression systems can be employed for the production of proteins using promoters of the invention. One such expression system employs a dihydrofolate reductase (DHFR) gene which is introduced into the vector comprising a promoter of the invention or a variant thereof operably linked to, a heterologous nucleic acid. Alternatively, an expression vector expressing DHFR can be co-transfected into the host cell, if a DHFR-deficient cell is used for expression. When increasing concentrations of methotrexate (MTX), a competitive inhibitor of the essential enzyme DHFR, are applied to the transfected cells, only cells with higher expression levels of DHFR survive. As MTX levels are increased further, only cells which amplify the copy number of the DHFR gene survive. In this way, by increasing the copy number of the vector comprising the promoter, increased expression of the heterologous nucleic acid can be achieved, thereby leading to increased protein production. A second expression system employs a glutamine synthetase (GS) gene that is introduced into the vector comprising a promoter of the invention or a variant thereof operably linked to a heterologous nucleic acid. Addition of a competitive inhibitor of GS, e.g., methionine sulphoximine (MSX), is used for increasing the copy number of the vector leading to increased protein production.

Any suitable prokaryotic or eukaryotic expression system can be used for expression of proteins using promoters of the invention. Examples of expression systems include, but are not limited to, plant, baculovirus, yeast, bacterial, drosophila, mammalian and cell free expression systems. Standard methods for introducing expression vectors into mammalian, bacterial, yeast, insect and plant cells are provided, for example, by Ausubel (1995), supra.

In certain embodiments, promoters of the invention and variants thereof are used in methods of gene therapy. For example, a promoter of the invention or a variant thereof is cloned into a viral or a non-viral gene therapy vector such that it is operably linked to a gene of interest. The promoter drives expression of the gene encoding a therapeutic protein when the vector is delivered to a subject, e.g., a human patient.

The following examples provide illustrative embodiments of the invention. One of ordinary skill in the art will recognize the numerous modifications and variations that may be performed without altering the spirit and scope of the present invention. Such modifications and variations are encompassed within the scope of the invention. The examples do not in any way limit the invention.

EXAMPLES

The following describes materials and methods used in the subsequent Examples.

A. Culturing of CHO-K1 Cells

CHO-K1 cells were obtained from American Type Culture Collection (Manassas, Va.) (ATCC No. CRL-9618). Cells were cultured in 250 ml spinner cultures containing 15 g/L DE-52 microcarriers (Whatman, Kent, UK) in 925 cell culture medium supplemented with 10% donor calf serum (DCS) (Invitrogen). Cells were maintained at 37° C. using a 20-40% $O_2$ and 5% $CO_2$ overlay and agitated at approximately 60 rpm for six days. Following growth of cells in the presence of serum, cultures were subjected to a daily 80% (v/v) replacement with serum-free 925 medium. Cells were grown in serum-free medium for 11 days prior to extraction of RNA from cells. For the determination of mRNA half-life, 7 mg/L of actinomycin D was added to the cultures in the serum-free phase.

B. RNA Extraction and Analysis

RNA was isolated from CHO-K1 cells using the RNAgents kit from Promega (Madison, Wis.). Gene expression was analyzed by Northern blotting. For Northern blot analysis, 5 μg of RNA was separated by electrophoresis on a denaturing glycoxal/dimethylsulfoxide gel using a NorthernMax®-Gly kit. (Ambion, Austin, Tex.). The RNA was subsequently transferred to nylon membranes (Schleicher & Schuell, Dassel, Germany). The blots were probed with the following gene probes amplified by PCR: galectin (GenBank® Accession No. M96676, nt 14-383); β-actin (Genbank® Accession No. U20114, nt 238-381); EF-1 (GenBank® Accession No. D00522, nt 7-192); rpS21 (GenBank® Accession No. X79059, nt 68-340); ferritin (GenBank® Accession No. M99692, nt 182-303) or a commercially available glyceryldehyde 3-phosphate dehydrogenase. (GAPDH) fragment (Ambion, Austin, Tex.). Each PCR product was radiolabeled by random priming. PCR primers used for amplification of each of the genes are listed in Table 1.

TABLE 1

| Gene | Primer | Sequence | SEQ ID NO: |
| --- | --- | --- | --- |
| β-actin | forward | GCTCTTTCTTCGCCGCTCC | 8 |
| β-actin | reverse | ACCACCCTCCAGCCTTCCC | 9 |
| EF-1 | forward | GAACGCAGGTGTTGTGAAAA | 10 |
| EF-1 | reverse | CTCGGCAGCCTCCTTCT | 11 |
| rpS21 | forward | GTGGACCTGTACGTGC | 12 |
| rpS21 | reverse | TTCTCACTTTTATTTATGAC | 13 |
| ferritin | forward | CGCCAGAACTACCACCAGGAC | 14 |
| ferritin | reverse | TTCAGAGCCACATCATCCCG | 15 |
| galectin | forward | TGGTCGCAAGCAACCTGAATC | 16 |
| galectin | reverse | TTGAAGTCACCGTCTGCCGC | 17 |

C. Transfection of CHO-K1 Cells

For transient transfection, CHO-K1 cells were plated on 6-well plates in 925 medium with 10% fetal bovine serum (FBS) (Invitrogen). The cells were grown to 50-75% confluency prior to transfection using Lipofectamine™ (Invitrogen). The pDsRED-1 plasmid (Clontech, Palo Alto, Calif.) was co-transfected with the pSV40-CD20 plasmid, which encodes a cell surface CD20 marker used to identify transfected cells. This pDsRED-1 plasmid encodes a Discosoma striata red fluorescent protein (RFP), the expression of which can be detected by FACS. Transfections were performed as per manufacturer's instructions. Briefly, cells were incubated with lipid-DNA complexes for 16 hrs in serum free Opti-MEM™ medium (Invitrogen). The medium was replaced with 925 medium with 10% FBS, and cells were harvested 48 hours post-transfection.

D. Fluorescence-Activated Cell Sorting Analysis

For FACS analysis, $1 \times 10^6$ cells were trypsinized and washed with cold PBS containing 2% FBS. Cells were subsequently incubated with an FITC-labeled anti-CD20 antibody (Pharmingen, San Diego, Calif.) for 30 minutes on ice. Cells were then washed with cold PBS containing 2% FBS and resuspended in 1 ml of cold PBS/2% FBS. FACS analysis was performed using FACSCalibur™ (BD Biosciences, San Diego, Calif.). All CD20-positive events were evaluated for their red fluorescent protein mean fluorescence intensity to assess promoter strength.

E. ASM Assay

Media from cells transfected with a vector encoding acid sphingomyelinase (ASM) were incubated at 37° C. with the synthetic substrate 2-(N-hexadecanoylamino)-4-nitrophenylphosphorylchlorine (Calbiochem, San Diego, Calif.) at the concentration of 12.5 mM in 250 mM sodium acetate, pH 5.5, containing 0.1 mM zinc acetate, 0.25 mg/ml bovine serum albumin (BSA) and 0.15% Tween 20. The reactions were stopped by the addition of 0.2 M glycine-NaOH containing 50% ethanol. The activity or amount of ASM was measured by the amount of 2-(N-hexadecanoylamino)-4-nitrophenolate produced using a calorimetric assay by measuring optical density at 415 nm.

F. GM Assay

Media from cells transfected with a vector encoding α-glucosidase (GAA) were incubated at 37° C. with the synthetic substrate p-nitrophenyl-D-a-glucopyranoside (Sigma, St. Louis, Mo.) at a concentration of 40 mM in 50 mM sodium acetate, pH 4.3, containing 0.1% bovine serum albumin (BSA). The reactions were stopped by the addition of 0.3 M glycine, pH 10.6. The activity or amount of GM was measured by the amount of p-nitrophenyl produced using a calorimetric assay by measuring optical density at 400 nm.

Example 1

Identification of the β-Actin Promoter in CHO-K1 Cells

Serial Analysis of Gene Expression (SAGE) was used to analyze the entire transcription profile of CHO-K1 cells that were grown in a serum-free perfused spinner culture.

The first step in SAGE involved synthesis of double stranded DNA from mRNA isolated from CHO-K1 cells using standard techniques. The cDNA was subsequently cleaved with a restriction endonuclease NlaIII, also called an anchoring enzyme, which is expected to cleave most transcripts at least once. The 3' portion of each cleaved cDNA was isolated by binding to streptavidin beads. The cDNA pool was then divided in half and ligated via anchoring the restriction site to a linker containing a type II restriction endonuclease site (for example, FokI). Type II restriction endonucleases cleave at a defined distance up to 20 base pairs away from their asymmetric recognition sites. The type II enzyme is typically called a tagging enzyme. Cleavage of the ligation product with the tagging enzyme results in the release of the linker with short pieces of the cDNA. A combination of the anchoring and tagging enzymes yields a 10 base pair tag which is unique to a gene.

Using this approach, sequence tags for each gene were represented by the 3'-most NlaIII site followed by a unique 10 bp sequence. In instances where tags could not be assigned to known genes, a SAGE library cDNA was PCR amplified using the SAGE tag and a commonly used M13 forward primer (GTTTTCCCAGTCACGAC, SEQ ID NO:18). PCR products were subsequently cloned into the pCR2.1 vector (Invitrogen) and sequenced using standard techniques. Identification of genes was based on the homology of the sequence of PCR products to known sequences in GenBank® (www.ncbi.nlm.nih.gov/genbank).

A BLAST® alignment (www.ncbi.nlm.nih.gov/blast) of nucleotide sequences to their mouse and/or rat counterparts was performed to identify the gene from which the tag was derived. Of the sixteen most abundant tags identified in this analysis (Table 2), the gene for all but one tag was identified. Of these fifteen identified genes, five were mitochondrial in origin and three were nuclear repetitive elements. Occurrence of multiple copies of these genes in each cell was the likely cause of their abundance in the SAGE output. Such sequences were not considered for further evaluation.

TABLE 2

| Abundance | Tag | Gene | SEQ ID NO: | Identified |
|---|---|---|---|---|
| 38 | CATGGAAGCAGAAT | Alu Repeat | 19 | J00052 |
| 33 | CATGCAGGAGCTTC | Mito COX I | 20 | PCR |
| 27 | CATGGGGGAGCGTT | Ribosomal Protein S21 | 21 | PCR |
| 27 | CATGGTACTGACAC | Mito COX III | 22 | PCR |
| 20 | CATGGCCTCCAAGG | GAPDH | 23 | X52123 |
| 20 | CATGATAATACGTA | Mito ATPase 6 | 24 | M14311 |
| 19 | CATGCCTTTAATCC | B-1 Repeat | 25 | PCR |
| 18 | CATGAATCGGAGGC | Mito Cytochrome B | 26 | J01436 |
| 18 | CATGAGGCAGACAG | EF-1 | 27 | D00522 |
| 18 | CATGGCGGCAGACG | Galectin (L-14) | 28 | M96676 |
| 16 | CATGGTGGCTCACA | Alu Repeat | 29 | J00056 |
| 15 | CATGTTGGCTGCCG | Ferritin Heavy Chain | 30 | M99692 |
| 14 | CATGCCCTGTGCCG | No Match | 31 | |
| 13 | CATGAGAGCGAAGT | Ribosomal Protein L41 | 32 | X82550 |
| 13 | CATGAGGAGGCCTA | Mitochondrial NADH Dehydrogenase | 33 | PCR |
| 12 | CATGCCCTGAGTCC | β-Actin | 34 | AF014363 |

Using this approach, promoters of four genes were identified as being the most active in CHO-K1 cells. These promoters were: β-actin, ribosomal protein S21 (rpS21), elongation factor 1 (EF-1), and glyceraldehyde 3-phosphate dehydrogenase (GAPDH). The high levels of these mRNAs in CHO-K1 cells could either be due to the promoter activity of their respective promoters or due to innate stability of the mRNAs. Although SAGE analysis provides a quantification of overall steady state levels for the mRNAs for genes, it does not distinguish between promoter activity of the gene and mRNA stability as the basis of the high expression of the mRNA. Thus, in order to distinguish between the two possibilities, half-life of mRNAs were measured. Briefly, expression of candidate genes was assessed by Northern blot analysis of CHO-K1 cells in spinner cultures at varying points following treatment of cells with actinomycin D.

Initially, the rpS21, GAPDH and EF-1 genes were analyzed and were all found to have relatively stable mRNAs with half-lives greater than 8 hours. These results suggested that the greater abundance of these mRNAs resulted from greater stability of the mRNAs and not necessarily greater activities of the respective promoters.

The half-life of galectin, ferritin, and β-actin mRNAs was also measured by Northern blot analysis, as described above, at 0, 4, 8, 10, and 15 hours following treatment of cells with actinomycin D. A representative Northern blot is shown in FIG. 6A. The relative mRNA levels are represented graphically in FIG. 6B. These data show that although both galectin and ferritin had half-lives of greater than 8 hours, the β-actin mRNA turned over more rapidly with a half-life of approximately 6 hours. Thus, the relative contribution of promoter strength to overall steady state mRNA levels was greater for β-actin than the other candidates in CHO-K1 cells. Accordingly, under these conditions, the β-actin promoter can be characterized as a strong promoter.

Example 2

Isolation and Characterization of the Hamster β-Actin and rpS21 Promoters

In light of the results described in Example 1, the candidate with the greatest abundance (rpS21) and the one with the most rapid mRNA turnover (β-actin) were selected for further study. A λ FIX II CHO-K1 genomic library (Stratagene, LaJolla, Calif.) was screened to isolate genomic DNAs for hamster β-actin and rpS21 promoters.

In order to isolate β-actin and rpS21 genomic clones, the *E. coli* bacterial strains, XL1-Blue MRA (P2) were grown in LB medium containing 10 mM magnesium sulfate and 0.2% maltose. The bacterial cells were pelleted and resuspended in 10 mM magnesium sulfate at an absorbance reading of 0.5 at 600 nm. Approximately one million phage from the library were incubated with the bacterial cells for 15 minutes at 37° C. Molten agarose was added to the phage/bacteria mixture and the bacteria were overlayed on agar-containing BioAssay plates (Nunc, Rochester, N.Y.). Following the hardening of the top agarose, the plates were inverted and grown at 30° C. overnight. Plates were subsequently chilled and overlayed twice with Genescreen Plus™ nylon filters (Perkin Elmer Life Sciences, Wellesley, Mass.). The nylon filters were denatured for 2 minutes in 0.1 M sodium hydroxide with 1.5 M sodium chloride and subsequently neutralized. Filters were UV cross-linked and probed.

A probe used for isolation of the hamster β-actin promoter was derived by random PCR from the 5' end of the β-actin gene (nt 238-381 of GenBank® Accession No. U20114). A probe used for the isolation of hamster rpS21 promoter was derived by PCR using primers set forth in SEQ ID NOs:12 and 13. Hybridizing phage for both β-actin and rpS21 promoters were purified using standard techniques. The DNA from the phage isolated from the phage lysates was purified by sequential extractions with chloroform, phenol, phenol/chloroform (1:1), and lastly, chloroform.

For isolation of hamster β-actin gene promoters, following ethanol precipitation, DNA was digested with restriction enzymes that had sites in the 5' portion of the β-actin hamster gene and subjected to Southern blotting using the same probe that was used to screen the genomic library.

Using this approach, an AvrII fragment of approximately 7 kb and a SalI fragment of approximately 5.5 kb were generated, both of which hybridized to the probe. These were subsequently cloned into pBluescript 11 KS plasmid (Stratagene). The 7 kb AvrII fragment has the ATCC Reference No. PTA-5309, deposited Jul. 3, 2003 with the American Tissue Culture Collection, P.O. Box 1549, Manassas, Va. 20108, U.S.A.

Plasmids containing AvrII and SalI fragments were digested with SfoI to remove the 3' end of the fragments which contained a portion of the open reading frame of the β-actin gene. These fragments were then cloned into the pDsRED-1 plasmid (Clontech) to create the constructs termed pDsRED-Avr (6.5 kb) and pDsRED-Avr (50.1 kb). In order to generate a construct containing all of intron 1 of the β-actin gene, PCR was performed using the following primers:

```
Forward:
AGGCCCAGCTTGGGACCAAGACAGAA         (SEQ ID NO:35)

Reverse:
CGCGGATCCGGCGAACTATATCAGGGC.       (SEQ ID NO:36)
```

The PCR fragment generated two products: a predicted product of approximately 7 kb and a smaller unexpected 3 kb product. Both of these PCR products were cloned into the pDsRED-1 plasmid (Clontech) to generate the constructs pDsRED-Avr(1)-7 and pDsRED-Avr(1)-3.

Each of the fragments of the β-actin hamster promoter that were cloned into the pDsRED-1 plasmid (Clontech) were transfected into CHO-K1 cells. The relative promoter strengths of each of the hamster β-actin promoter fragments were measured using FACS as described above. The results of the activity assays are summarized below.

Avr(1)-3 fragment of β-actin promoter which spans from nt −1970 to nt +1037 exhibited the highest promoter activity. The Avr(1)-7 fragment which spans from nt −6000 to nt +1037 exhibited an activity that was 47% of the activity exhibited by Avr(1)-3. The Avr(6.5 Kb), Sal(5.1 Kb), Actin(3 kb), and Actin-P(2.8 kb) fragments exhibited only 2%, 2%, 2%, and 0% promoter activity, respectively, as compared to the Avr(1)-3 fragment.

The Avr(1)-3 fragment was subsequently sequenced, and the sequence is set forth in SEQ ID NO:1. Additionally, the region 660 nt upstream of the 5' of Avr(1) 3 was also sequenced. This longer sequence from nt −2622 to nt +1037 is set forth in SEQ ID NO:7.

For isolation of the rpS21promoter, following isolation of DNA from the hybridizing phage, the DNA was amplified by POR using the following primers:

```
Forward:
AGCTCTAATACGACTCACTATAGGGC      (SEQ ID NO:40)

Reverse:
CTCTAGGCCAGCGGAGCGCAG.          (SEQ ID NO:41)
```

The PCR product was cloned into the vector PCR2.1 (Invitrogen) and subsequently sequenced. The nucleotide sequence of the hamster rpS21promoter is set forth in SEQ ID NO:39. The promoter was excised using EcoRI sites flanking the cloning sites and cloned into the pDsRED1-1 vector (Clontech). The 2 kb hamster rpS21promoter sequence has ATCC Reference No. PTA-6149, deposited Aug. 5, 2004, with the American Tissue Culture Collection, P.O. Box 1549, Manassas, VA 20108, U.S.A.

Example 3

Functional Comparison of the Hamster β-Actin and CMV Promoters

The promoter activity of Avr(1)-3 was compared to that of the CMV immediate early promoter (Invitrogen) and the human EF-1 promoter (Invivogen).

CHO-K1 cells were transiently transfected with either pDsRED-1 plasmid containing either Avr(1)-3, the CMV immediate early promoter upstream, or the human EF-1 promoter, each operably linked to the RFP gene. Expression of RFP was assessed by FACS 48 hours post-transfection.

As shown in FIG. 7A, in cells transfected with Avr(1)-3, the β-actin promoter sequence (SEQ ID NO:1) showed a higher level of RFP expression as compared to either the CMV or EF-1 promoters. In particular, expression was approximately two-fold higher with Avr(1)-3 than with the CMV promoter.

In order to determine whether this observed expression profile is sustainable in stable transfectants, transfected CHO-K1 cells were selected for two weeks with G418™. Expression of RFP in the surviving pools of cells was then assessed. As depicted in FIG. 7B, similarly to transient transfected cells, the highest RFP expression was observed in cells transfected with Avr(1)-3, the β-actin promoter sequence set forth in SEQ ID NO:1. Example 4: Activity of the Hamster β-Actin Promoter in BHK-21 and HEK293 cells The activity of the hamster β-actin promoter was compared to that of CMV promoter in BHK-21 (ATCC No. CCL 10) and HEK293 (ATCC No. CRL-1573) cells using stable transfection assays as described in Example 3. As seen previously in CHO-K1 cells, expression of RFP in BHK-21 cells was significantly higher when using the β-actin promoter instead of the CMV promoter (Table 3). In HEK293 cells, the hamster β-actin promoter resulted in expression of RFP at levels roughly equivalent to those of the CMV promoter.

TABLE 3

| Cell line | CMV promoter | β-Actin promoter |
|---|---|---|
| BHK-21 | 8.3 ± 0.4 | 121 ± 99.8 |
| HEK293 | 139 ± 9.9 | 102 ± 8.3 |

Example 5

Rat and Mouse β-Actin Promoters

Publicly available databases of nucleotide sequences were searched using default settings for potential homologs of the hamster β-actin promoter sequence set forth in SEQ ID NO:1.

The 5' portion of a β-actin hamster gene (GenBank® Accession No. U21104; SEQ ID NO:4) exhibits 98% identity to the 3' portion of the hamster β-actin promoter sequence. This homology, however, is only 40% over the entire length of the hamster β-actin promoter sequence set forth in SEQ ID NO:1. No promoter activity is known for this portion.

Previously known β-actin promoters: human (GenBank® Accession No. gi28337A) and chicken (GenBank® Accession No. gi2170437) were aligned with the hamster β-actin promoter for homology determination with the BLAST® program using default settings. The human and the chicken β-actin promoter sequences had only 10% and 1% identity, respectively, to the hamster β-actin promoter (SEQ ID NO:1).

A rat (Rattus norvegcus) genomic supercontig (GenBank® Accession No. NW_042778) was identified on chromosome 12 of the rat genome as containing a nucleotide sequence having a 67% identity over the entire length of SEQ ID NO:1.

Similarly, a contig (GenBank® Accession No. NT_039324) was identified on chromosome 5 of the mouse (Mus musculus) genome as having a 80% identity over the entire length of SEQ ID NO:1.

Figure 1F:
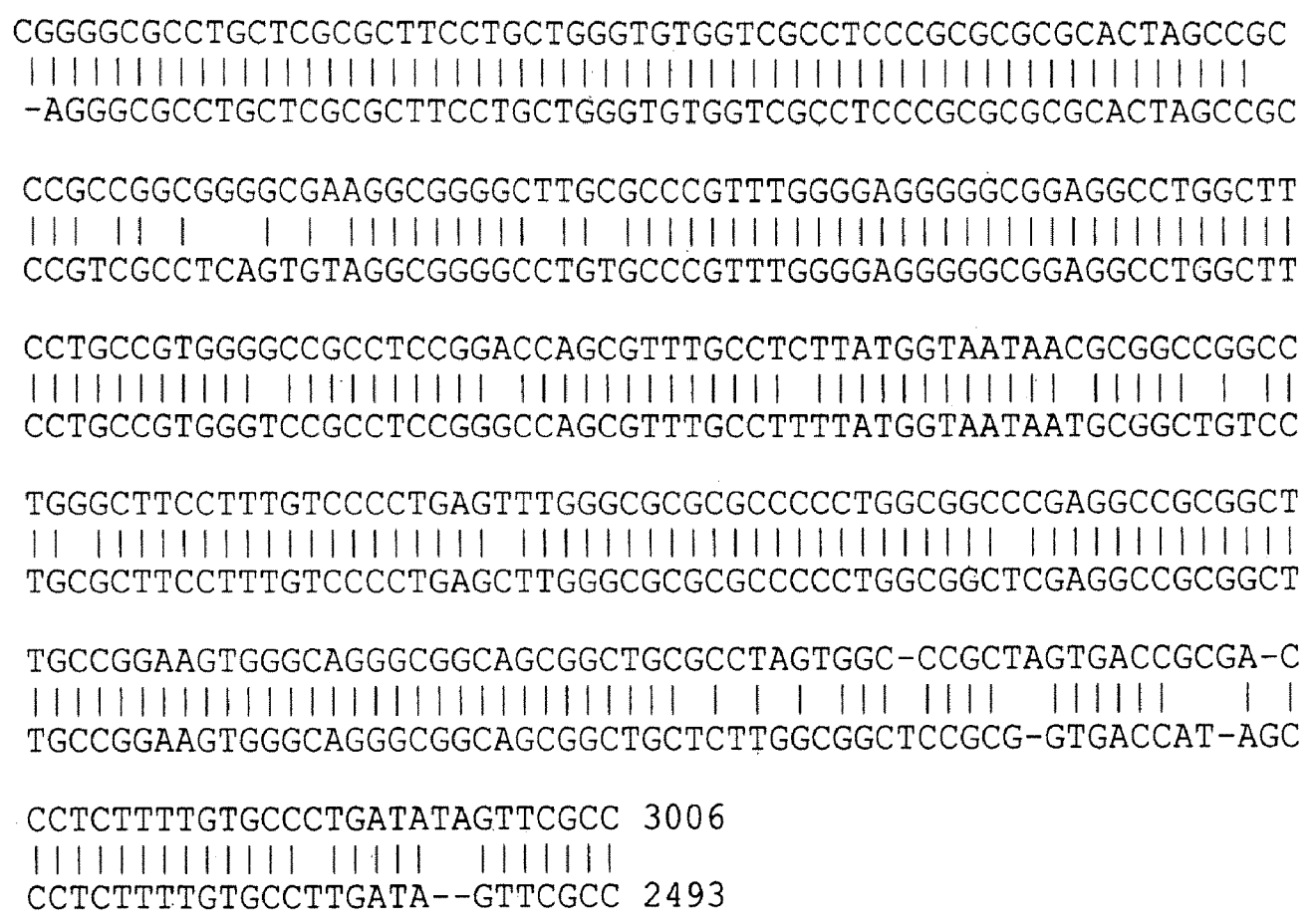
Figure 2D:
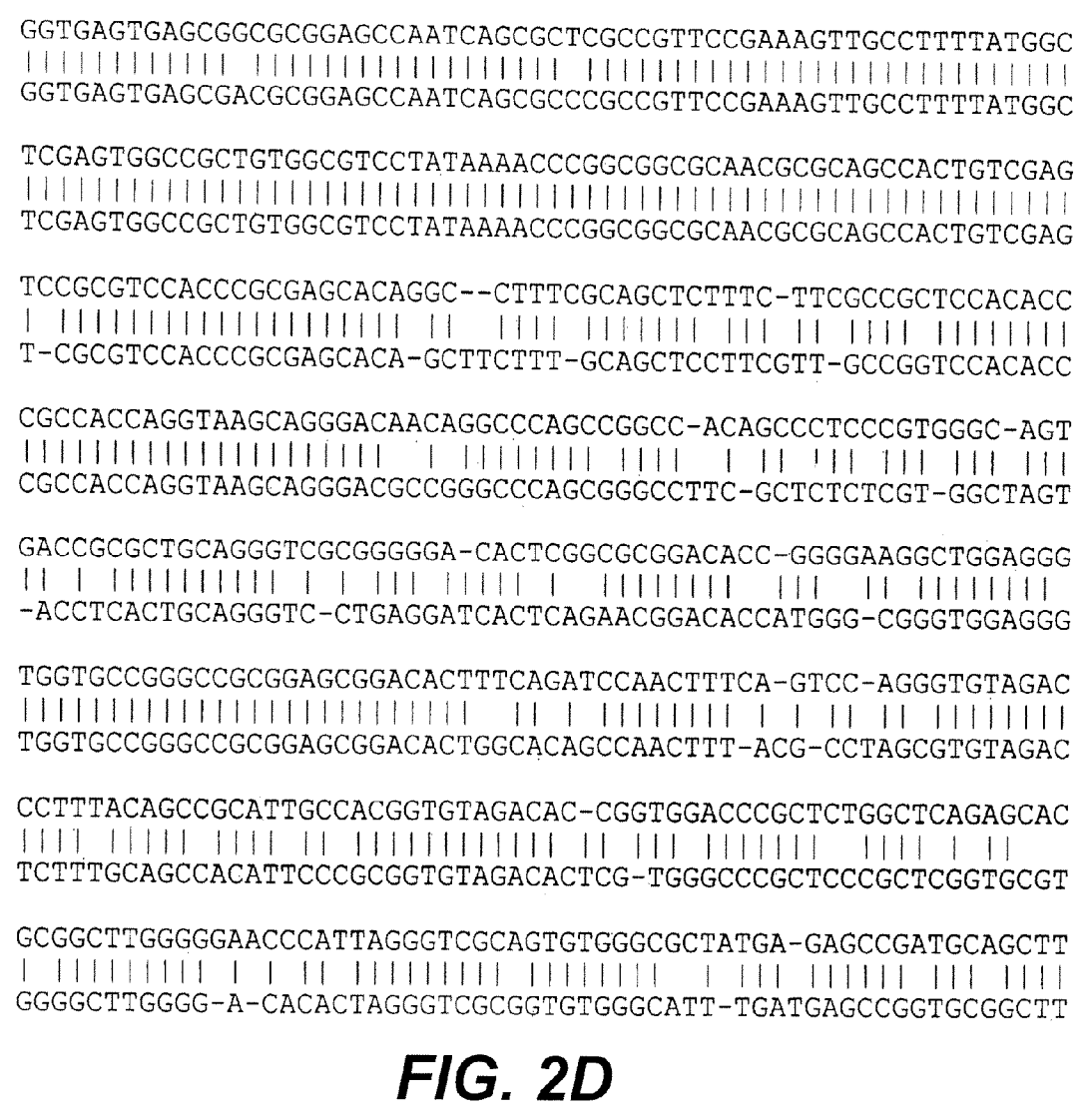
Figure 2F:
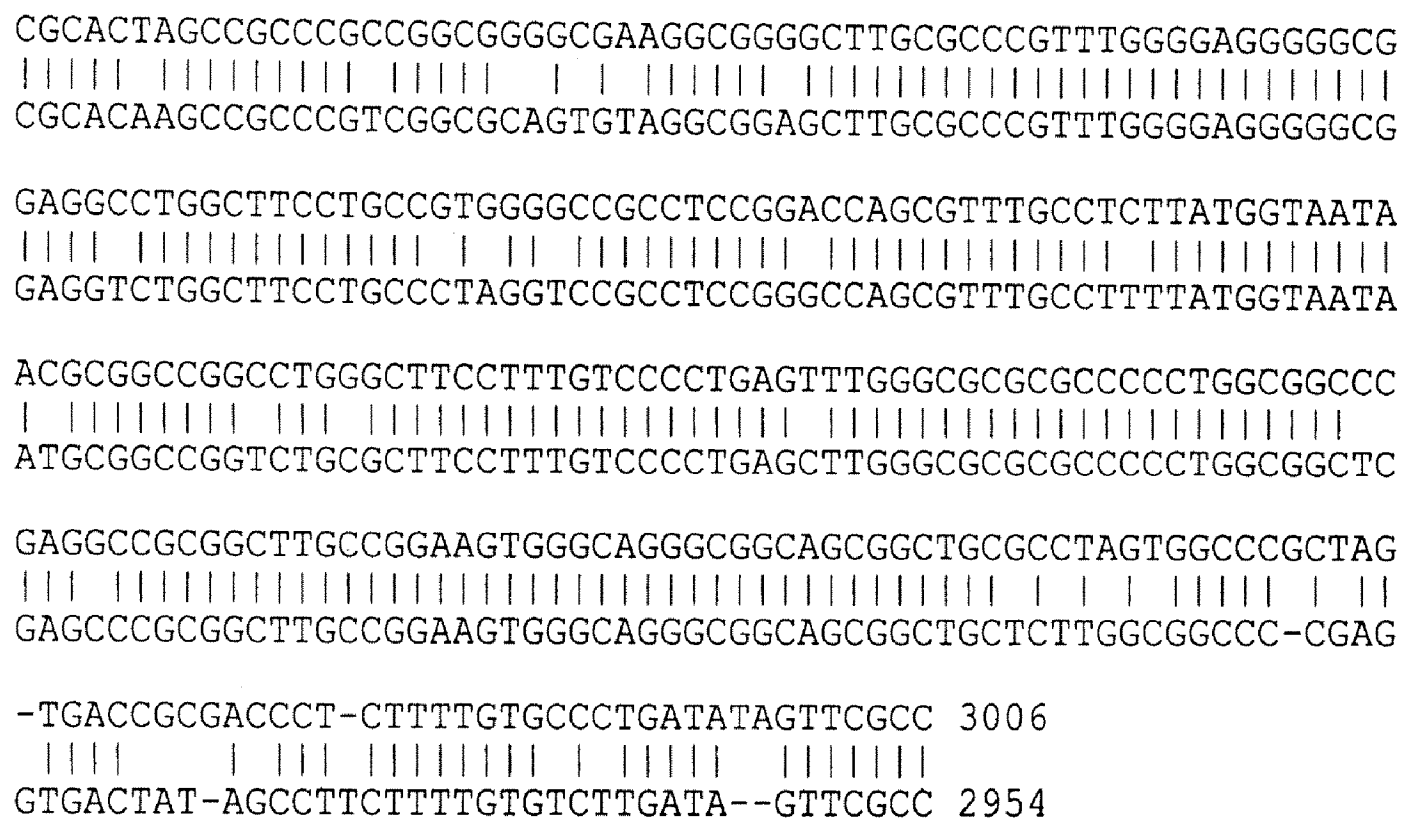

The sequence alignments of hamster β-actin promoter sequence (SEQ ID NO:1) with the hamster gene sequence, and β-actin promoters from human, chicken, rat and mouse are depicted in FIGS. 3, 4, 5, 1, and 2, respectively.

Example 6

Activities of the Rat and Mouse β-Actin Promoters

The rat and the mouse promoter sequences set forth in SEQ ID NOs:2 and 3, respectively, are cloned into the pDsRED-1 plasmid (Clontech). The CMV promoter is also cloned upstream of the RFP gene in the pDsRED-1 plasmid. These plasmids are transfected into CHO-K1 cell, or another cell line. Expression of the RFP is assessed by FACS 48 hours post-transfection.

Cells transfected with the rat or the mouse β-actin promoter are expected to show a higher RFP expression than the CMV promoter under similar conditions.

Example 7

Expression of Proteins Using Hamster β-Actin Promoter

To further evaluate activity of the hamster β-actin promoter, an expression system utilizing dihydrofolate reductase (DHFR) selection and methotrexate (MTX) amplification was used. The vector pGZ6 was derived from the pQLHAXSV2DHFR plasmid, so as to contain the 3 kb hamster β-actin promoter (SEQ ID NO:1) in addition to a DHFR gene under the control of the SV40 early promoter. The pCLHAXSV2DHFR plasmid has been previously described by Cole et al. (1993) Biotechnology, 11:1014-1024. Briefly, the metallothionine (MT) promoter in the pCLHAXSV2DHFR vector was replaced with the β-actin promoter to create the pGZ6 vector. cDNAs for two proteins of therapeutic interest, acid sphingomyleinase (ASM) and α-glucosidase (GAA) were operably linked to the hamster β-actin promoter. The ASM cDNA was obtained through the IMAGE™ consortium (GenBank® Accession No. AI587087). The cDNA for GAA was obtained from Dr. Martinuik at the New York University School of Medicine. The nucleotide sequences of the ASM and GAA cDNAs are set forth in SEQ ID NOs:37 and 38, respectively. Similarly, the two cDNAs were also cloned downstream of the CMV promoter in a vector containing the same DHFR expression cassette. The DHFR-deficient CHO-K1 cell line DXB11 was transfected in triplicate with both sets of expression vectors. After two weeks of selection in nucleotide-deficient media containing 20 nM MTX, a heterogeneous uncloned pools of cells were washed with PBS and transferred to serum-free media. Twenty four hours later, levels of ASM or GAA in the media were measured.

The results of one such experiment are demonstrated in FIGS. 8A and 8B. The levels of ASM generated from the hamster β-actin promoter in the stable pools were from 2 to 15 times greater than with the CMV promoter, and in the case of the GM pools, 2 to 5 times greater.

The stable pools were further used to evaluate the ability of the β-actin promoter to sustain long-term protein expression. Typically, for industrial production of proteins, high expression is achieved by selecting cells with a higher gene copy number through a process that involves increasing the number of selection steps and/or concentration of MTX. In order to determine whether a higher expression could be achieved via this strategy with the β-actin promoter (SEQ ID NO:1), the ASM pools initially selected at 20 nM MTX were amplified by selection for two weeks at ten-fold higher levels of MTX (200 nM). As summarized in Table 4, two of the three tested β-actin pools showed 2 to 3-fold greater levels of ASM after amplification relative to the starting 20 nM pools. In contrast, only one of the CMV pools tested showed higher levels than the 20 nM pool, from which it was derived. Among the six ASM pools generated with either of the two promoters, the highest expressing β-actin pool generated six times the amount of ASM obtained with the highest expressing pool generated with CMV promoter. This demonstrates that, at least under the conditions tested, the hamster β-actin promoter is superior to the CMV promoter.

TABLE 4

| Pool | Expression of ASM at 20 nM MTX | Expression of ASM at 200 nM MTX |
| --- | --- | --- |
| CMV-ASM Pool A | 4.3 | 8.2 |
| CMV-ASM Pool B | 16.9 | 9.5 |
| CMV-ASM Pool C | 3.6 | 3.7 |
| β-actin-ASM Pool A | 33.5 | 100.0 |
| β-actin-ASM Pool B | 59.3 | 27.9 |
| β-actin-ASM Pool C | 45.6 | 90.5 |

In a separate experiment, the hamster β-actin promoter was used for expressing tissue plasminogen activator (tPA) protein, which is a thrombolytic agent used in patients for dissolving blood clots. CHO-DXB11 cells were transfected with a pGZ6-tPA expression vector in which the hamster β-actin promoter is operably linked to the tPA gene. Stable transfectants were selected by growth in nucleotide deficient medium containing 200 nM MTX. The resulting pool of uncloned cells was then subjected to 500 nM MTX to amplify transgene copy number. This pool of cells was removed from MTX, expanded and seeded on Cytopore™ 2 microcarriers in a 1 liter spinner culture. Cells were grown for 7 days in a serum containing medium. For the next 4 days, the serum was removed by daily 80% exchanges with serum free medium. Media harvests were then collected over 15 days and analyzed for tPA expression using a commercially available ELISA kit (TintElize® tPA kit, Biopool International, Inc., Ventura, Calif.). As depicted in FIG. 9 of this experiment, the use of the hamster β-actin promoter resulted in tPA expression at a concentration of about 30 mg/L per day. This result compares favorably to recently published reports in which about 30-40 mg/L of tPA was produced after 0.4-8 days using other promoters (Senger et al. (2003) Biotechnology Progress 19: 1199-1209; Dowd et al. (2000) Biotechnology Progress 16:786-794).

Example 8

Production of Antibodies Using Hamster β-Actin Promoter

In order to produce an antibody to a TGF-β family member, nucleic acid encoding either an anti-TGF-β antibody light chain or an anti-TGF-β antibody heavy chain is cloned downstream of the hamster β-actin promoter in two separate pGZ6 expression vectors.

The DHFR-deficient CHO-K1 cell line DXB11 is transfected in with both expression vectors. After two weeks of selection in nucleotide-deficient media containing MTX, levels of anti-TGF-β antibody, including both the light chain and the heavy chain, are measured in the media.

Example 9

Expression of Proteins Using Hamster rpS21 Promoter

The hamster rpS21 promoter activity was compared to the hamster β-actin promoter activity for expression in CHO-DXB11 cells. CHO-DXB11 cells were transfected with expression vectors containing human α-glucosidase (rhGAA) operably linked to either the hamster rpS21 promoter of SEQ ID NO:39 (pGZ3IC-GAA) or hamster β-actin promoter of SEQ ID NO:1 (pGZ6IC-GAA). In both cases the rhGAA gene was linked to the gene encoding a cell surface marker (CD20) through an internal ribosome entry site (IRES) sequence. After selection of cells with 0.2 μM MTX in nucleotide deficient medium, the cells were labeled with a FITC-conjugated antibody to CD20 and sorted by FACS for high expressing clones. Selected cells were plated in 96-well plates and expanded for evaluation of rhGAA expression. 38 clones were analyzed for the hamster rpS21 promoter, and 29 clones were analyzed for the hamster β-actin promoter. Table 5 shows the distribution of expression ranges in the resulting clones for both promoters.

TABLE 5

| Vector | GAA Expression <2 pg/cell/hr | GAA Expression 2–5 pg/cell/hr | GAA Expression 5–8 pg/cell/hr | GAA Expression 8–10 pg/cell/hr |
| --- | --- | --- | --- | --- |
| pGZ3IC-GAA | 16% | 50% | 26% | 8% |
| pGZ6IC-GAA | 52% | 34% | 14% | 0% |

In a separate experiment, the hamster rpS21 promoter was used for expressing ASM in CHO-DXB11 cells. The activity of the rpS21 promoter was compared to activities of both β-actin and CMV promoters. CHO-DXB11 cells were transfected in triplicate and either selected directly at 200 nM MTX, or initially selected at 20 nM MTX and then amplified for two weeks at 200 nM MTX, as discussed in Example 7. Levels of ASM were measured in the media as described. ASM expression in untransfected cells was undetectable.

As summarized in Table 6, all three rpS21 pools showed 2- to 3-fold greater levels of ASM after amplification relative to the starting 20 nM pools, from which they were derived. Further, the levels of ASM generated were higher than the levels generated with the CMV promoter (Example 7).

TABLE 6

| Pool | Expression of ASM nU/cell/24 hr (at 20 nM MTX) | Expression of ASM nU/cell/24 hr (at 200 nM MTX) |
| --- | --- | --- |
| rpS21-ASM Pool A | 12 | 34 |
| rpS21-ASM Pool B | 13 | 30 |
| rpS21-ASM Pool C | 16 | 41 |

The levels of ASM expression generated with selection of the pools directly at 200 nM MTX are summarized in Table 7.

TABLE 7

| Pool | ASM Expression |
| --- | --- |
| CMV-ASM Pool A | 38 |
| CMV-ASM Pool B | 193 |
| CMV-ASM Pool C | 44 |
| β-actin-ASM Pool A | 381 |
| β-actin-ASM Pool B | 125 |
| β-actin-ASM Pool C | 515 |
| rpS21-ASM Pool A | 342 |
| rpS21-ASM Pool B | 60 |
| rpS21-ASM Pool C | 51 |

The levels of ASM generated from the hamster rpS21 promoter at 200 nM MTX were on average about 1 to 2 times greater than that with the CMV promoter. The ASM levels generated from the β-actin promoter, on the other hand, were on average about 3 to 4 times greater than that with the CMV promoter. Thus, the rpS21 promoter was at least as active as the β-actin promoter when used for expressing GAA, however, it exhibited lower activity than, the β-actin promoter when used to express ASM. Both promoters, however, were more active than the CMV promoter.

The specification is most thoroughly understood in light of the teachings of the references cited within the specification which are hereby incorporated by reference. The embodiments within the specification provide an illustration of embodiments of the invention and should not be construed to limit the scope of the invention. The skilled artisan readily recognizes that many other embodiments are encompassed by the invention. All publications and patents cited and sequences identified by accession or database reference numbers in this disclosure are incorporated by reference in their entirety. To the extent the material incorporated by reference contradicts or is inconsistent with the present specification, the present specification will supercede any such material. The citation of any references herein is not an admission that such references are prior art to the present invention.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may very depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

The invention claimed is:

1. An isolated nucleic acid sequence comprising a nucleotide sequence that has promoter activity and is at least 95% identical to the nucleotide sequence set forth in SEQ ID NO:1 over the entire length of SEQ ID NO:1.

2. A vector comprising the promoter of claim 1.

3. The vector of claim 2, wherein the promoter is operably linked to a heterologous nucleic acid encoding a protein.

4. The vector of claim 3, wherein the heterologous nucleic acid encodes a therapeutic protein.

5. The vector of claim 4, wherein the therapeutic protein is selected from the group consisting of acid sphingomyelinase (ASM), α-glucosidase (GAA), and tissue plasminogen activator (tPA).

6. An isolated host cell transfected with the vector of claim 2.

7. The host cell of claim 6, wherein the host cell is a Chinese hamster ovary (CHO) cell.

8. A method of producing a protein comprising:
(a) culturing a host eukaryotic cell transfected with the vector of claim 3; and
(b) recovering the protein.

9. The method of claim 8, wherein the protein is an antibody.

10. The method of claim 9, wherein the antibody binds to a TGF-β family member.

11. The method of claim 10, wherein the protein is a therapeutic protein.

12. The method of claim 11, wherein the therapeutic protein is selected from the group consisting of acid sphingomyelinase (ASM), α-glucosidase (GAA), and tissue plasminogen activator (tPA).

13. The method of claim 11, wherein the therapeutic protein is selected from the group consisting of insulin, thyrogen stimulating hormone, erythropoietin, glucocerebrosidase, and α-galactosidase.

14. The method of claim 8, wherein the host eukaryotic cell is a mammalian cell.

15. The isolated nucleic acid sequence of claim 1, comprising the nucleotide sequence of ATCC Deposit No. PTA-5309.

16. The isolated nucleic acid sequence of claim 1, wherein the nucleotide sequence that has promoter activity is at least 97% identical to the nucleotide sequence set forth in SEQ ID NO:1 over the entire length of SEQ ID NO:1.

17. The isolated nucleic acid sequence of claim 16, wherein the nucleotide sequence that has promoter activity is at least 99% identical to the nucleotide sequence set forth in SEQ ID NO:1 over the entire length of SEQ ID NO:1.

* * * * *

SEQUENCE LISTING

<160> NUMBER OF SEQ ID NOS: 41

<210> SEQ ID NO 1
<211> LENGTH: 3007
<212> TYPE: DNA
<213> ORGANISM: Artificial Sequence
<220> FEATURE:
<223> OTHER INFORMATION: beta-actin promoter isolated from CHO cells

<400> SEQUENCE: 1

```
gggaccaaga cagaaccata agccagtggg atagatcaga aatgttccag aggtgggatg      60
gggccagagt gcctgcccct tgaaccgtcc cagggaccag aggtgacaaa gtggcaacac     120
aggtcctgcc tgggaatctg gtctgctcct acttagtaaa gctgcctggt gtcacacaag     180
aggcccccac ttattcctgc accoctggtg gtaggtggcg tcttctcccc tgcagccacc     240
aggctcccct gagaacactg ccggcagtcc tcattgacag gcagtattcg ctctgcccca     300
cccccacctg tgaattgcag ggctggcagg tcctcaggca gctggcaaac cgcctgaaca     360
actgagagat acagggccag ggccagggca gtcccgtccc ccggaggcag ggaggggacg     420
tgctgggaaa gttctctctc tcaggcccag gttggtgact gcagaaggct tctgtcaaat     480
ctcttttgtg ggaaccacag agtagccctg aacgtggggg tgtgcttcca gtatactctg     540
```

```
gggtcaccct ttccatactg gaggcctctg caacttcaaa atgctctgct accaacctag      600
cacaaggaag ttggtccagc ctccccacgc agggccactg ctgcagtcca tatatggact      660
aagccttcct tggtttcaac acctacactc actgagcccc tactatgtgt atgcagagcc      720
gagacaggcc cgagcatctc atctgaagca cccttcttgc ctaaattcag ttttctgtca      780
ctttctccca ggaggtgtgt gtccctctaa gctaagccag gggtccctca cccctgcccc      840
actcccatcc ctagtgtagg tatcagctga agagcttcct gagcagaaca ctcttgggtg      900
ctgacatttt gataaatagg cccatgttta ggagagcagg ggtccggggg cgggagatct      960
tctctggtgg attgagggct ccaagaacta ctctttgagc acgctgcccc tcccagagtc     1020
cccacagcct ccagatggac tagaacacag ttcggctgtg gctgcacata actaacagag     1080
gatagatggt gggtcccagc ccaacagtgc ctggcaatca cccagagcca ccagctaacg     1140
gccttggctt agttttttgc ctgggtgtga tcaggcagcc ctccaaaact gcccggactc     1200
catgacaagt tttgcttgtt ctatagcaca cagttccttt ctaggtctgg ggcaagggac     1260
atcgggagac atcttcctgc aacagctcca gtcactggac caccaggctc gccctgtctt     1320
tggtgtgtgg ccctgagtct cctaagtggc caaacctgt gaagacccct ccaaccacag      1380
ttttgcttct aaattgtacc ccaacacacc tagcaaattg aaaccccacc agaagtcccc     1440
cagatctggc tttccggcta ttgctggcaa ggggagtga ctcccggccc attcaatcca      1500
ggccccgcgt gttcctcaaa caagaagcca cgtaaacata aaccgagcct ccatgctgac     1560
ccttgcccat cgaggtactc aatgttcacg tgatatccac acccgagggt cctggggtg      1620 ggtgcatgag ccccagaatg caggcttgat aaccgagacc ctgaatcggg cagtgtccac     1680
aagggcggag gcccagtcat gcatgttcgg gcctatgggg ccagcaccca acgccaaaac     1740
tctccatcct cttcctcaat ctcggctttc tctctctctc tcttttttt tttttatttt      1800 ttttttttgc aaaaggaggg gagagggggt aaaaaaatgc tgcactgtgc ggctaggccg     1860
gtgagtgagc ggcgcggagc caatcagcgc tcgccgttcc gaaagttgcc ttttatggct     1920
cgagtggccg ctgtggcgtc ctataaaacc cggcggcgca acgcgcagcc actgtcgagt     1980
ccgcgtccac ccgcgagcac aggcctttcg cagctctttc ttcgccgctc cacacccgcc     2040
accaggtaag cagggacaac aggcccagcc ggccacagcc ctcccgtggg cagtgaccgc     2100
gctgcagggt cgcgggggac actcggcgcg gacaccgggg aaggctggag ggtggtgccg     2160
ggccgcggag cggacacttt cagatccaac tttcagtcca gggtgtagac cctttacagc     2220
cgcattgcca cggtgtagac accggtggac ccgctctggc tcagagcacg cggcttgggg     2280
gaacccatta gggtcgcagt gtgggcgcta tgagagccga tgcagctttc gggtgttgaa     2340
ccgtatctgc ccaccttggg gggaggacac aaggtcggga gccaaacgcc acgatcatgc     2400
cttggtggcc catgggtctt tgtctaaacc ggtttgccca tttggcttgc cgggcgggcg     2460 ggcgcggcg gcccggctcg gccgggtggg ggctgggttg ccactgcgct tgcgcgctct     2520
atggctgggt attggggcgc gtgcacgctg gggagggagc ccttcctctt cccctctcc      2580 caagttaaac ttgcgcgtgc gtattgagac ttggagcgcg gccaccgggg ttgggcgagg     2640
gcggggccgt tgtccggaag gggcggggtc gcagcggctt cggggcgcct gctcgcgctt     2700
cctgctgggt gtggtcgcct cccgcgcgcg cactagccgc ccgccggcgg ggcgaaggcg     2760
gggcttgcgc ccgtttgggg agggggcgga ggcctggctt cctgccgtgg ggccgcctcc     2820
ggaccagcgt ttgcctctta tggtaataac gcggccggcc tgggcttcct ttgtcccctg     2880
agtttgggcg cgcgccccct ggcggcccga ggccgcggct tgccggaagt gggcagggcg     2940
```

| | |
|---|---:|
| gcagcggctg cgcctagtgg cccgctagtg accgcgaccc tcttttgtgc cctgatatag | 3000 |
| ttcgccg | 3007 |

<210> SEQ ID NO 2
<211> LENGTH: 2493
<212> TYPE: DNA
<213> ORGANISM: Rattus norvegicus

<400> SEQUENCE: 2

| | |
|---|---:|
| tgtgggaaag ataaagtcgc tctgaacctg ggggtgtgtt tccagtatgc tggagtggtg | 60 |
| gtcacccttt ccagactgga ggcctctgca acttcaaaat gccctgccac aagcctagaa | 120 |
| caaggaagct ggtctggcct cctcatgcac agccactgta gcccatatat ggatgaagcc | 180 |
| ttccttggtt tcaacaccta cactttgtga gccagtgcac acctactatg catgtgtaaa | 240 |
| gccatggcag gtccagagca tcccacctga agcattctcc ttgcctaaat atagctttct | 300 |
| gtcactctct cccaggagtt gtgcgtcctt ctaagctaag ctgagggacc cgaccctcaa | 360 |
| ctctgatccc ctgctgtagc tatcagccaa atggctagct tcctgagcag aactctccta | 420 |
| cttaggtgag gagagcaggg ggttcttctc tctggaggat ttgggctct ggtgaccacc | 480 |
| agcacttccc tgagtagttt gtcactccca gagtccccgt ggccagcaga tgaacagttc | 540 |
| agtgtacagt tcagctgtgg ctgcacataa tacatagagg ctagatggtg ggctccagcc | 600 |
| caacgatgcc tggcagtcac ccagagccac tagctaacgg cccaggctta gtcttgcctg | 660 |
| ggtgtgatca ggcagccctc caaaagtgcc ggactccatg agaagttttg cttgttcgat | 720 |
| tgagcacagt tcctttctag gtccggggca gaggatatct ggaggcatct tcctgcaaca | 780 |
| aacacctcca gtcactggac caccggggct tgccctatcc ttgggactct ggccttgagt | 840 |
| ggtcaagatc cctgaagacc ttcccaacca cagctctgct tccaagttgt accccaacac | 900 |
| acctagcaaa ttagaactgc agcagaaggc ccccagatct ggctttcctg actattgcta | 960 |
| gcaaggggga gtgactctct gcccattcaa tccagacccc gtgtgtccct caaacaaaag | 1020 |
| gccactcaaa tagggtccgg gccttcaagc tgaccctcgc ccacttaggt gatcattatt | 1080 |
| cccgtgacat ccacacccag agggtcctgg ggtgggtggg tgaccccag aatacaggcc | 1140 |
| tagtaaccga gtcactgaat gggatagtgt ccacaagggc gggggctatt cttgtccatc | 1200 |
| tgggcctacg gaaccagcac ccatcgccaa actcttcatc ctcttcctca atctcgcttt | 1260 |
| ctctctcgct cgcttttttt tcttcttttt tttttttttt ttttttttt gcaaaaggag | 1320 |
| gggagagggg gtaaaaaaat gctgcactgt gcggcgaggc cggtgagtga cgacgcgga | 1380 |
| gccaatcagc gcccgccgtt ccgaaagttg ccttttatgg ctcgagtggc cgctgtggcg | 1440 |
| tcctataaaa cccggcggcg caacgcgcag ccactgtcga gtccgcgtcc accgcgagt | 1500 |
| acaaccttct tgcagctcct ccgtcgccgg tccacacccg ccaccaggta agcagggacg | 1560 |
| tcgggcccag cgggccccaa ctttaccttg gccactacct cgctgcagga tcgtgaggaa | 1620 |
| cactcagaag ggacaccgta gaggggtgga gcgtggtacc gggccgcgga gcggacactg | 1680 |
| gcaaagctta actttccgcc tagggtgtag agtgtttgca gtcgtattcc cgcggtgtag | 1740 |
| acactcgtgg gcacgctcct gcttggtgcg cggggcttgg ggacacacta gagtcgcggt | 1800 |
| gtgggcattt ggagagccgg tgcggcttgc gggtgttaag ccgcatctgt ccaccttgag | 1860 |
| gggacacagt attgggagtc aggcgttaca atcacgcttt gatggcctat ggtctttgt | 1920 |
| ccaaaccggt tttgcccatt cggcttggcg ggcgcggcgg ggccggctcg gccgggtggg | 1980 |

-continued

```
ggctgggatg ccattgcgcg tgcgcgctct atcactgggc attggggcgc gtgcgcgctg    2040
gggagggaac tcttcctctc ccctcttcc gagttaagag ttgcgcgtgc gtattgagac    2100
taggagcgcg gccgcccgg gttgggcgag ggcggggccg ttgcccggaa ggggcggggt    2160
cgtagcggct agggcgcctg ctcgcgcttc ctgctgggtg tggtcgcctc ccgcgcgcgc    2220
actagccgcc cgtcgcctca gtgtaggcgg ggcctgtgcc cgtttgggga ggggcggag    2280 gcctggcttc ctgccgtggg tccgcctccg gccagcgtt tgccttttat ggtaataatg    2340
cggctgtcct gcgcttcctt tgtcccctga gcttgggcgc gcgcccctg gcggctcgag    2400 gccgcggctt gccggaagtg ggcagggcgg cagcggctgc tcttggcggc tccgcggtga    2460
ccatagccct ctttgtgcc ttgatagttc gcc                                 2493
```

<210> SEQ ID NO 3
<211> LENGTH: 2953
<212> TYPE: DNA
<213> ORGANISM: Mus musculus

<400> SEQUENCE: 3

```
agaccagaat tgtttcagag gtcgggtggg gctgaggtgc ctgcccttg accagtccca      60 ggactgagag gtgacaaagt ggcaacacag gtcctgcctg gaatctggt ctgctctaac     120 ctagtaaagc tgtctggtgt cacccaagag gctccctcca catcctgcac ccctgatggc     180
tgatggcatc tttctccctt gcaccccacc agggttctcc tgggaatact ctgggctctc     240
cttattgaca ggcagcattt gccctgcccc accccacct gtgacttgca ggactggcag     300
gtccttgggc agctggcaaa ctgcctgagc aactgagaaa tacaaggcca gggccagggc     360
agtcctgtcc cccggaggca gggaggagac tgcctgggaa agttctctca gggttggtga     420
ctgcagaaga cttttgtcaa attttttttt ttttttttggt gggaaagata actagggtg     480 tgtttccagt tcacagcata tgctggggtg atggtcacct cttccagaca aggcctcagc     540
aacttcaaaa tgccctgcca ccagccaaga acaaggaagc tggccactgt agtccatata     600
tggatgaagc cttctttggt ttcaacacct acactttgtg agccagtgaa cacctaccta     660
tgcatgcact gaggcacggc aggcccagag catctcacct gaagcaccct tcttgcctaa     720
atccagcttt ctgtcacact ctcccagaag gtgcgtgtcc ttctaagcta agctgaggga     780
tccggccctc aaccctgacc ccgtgtgtag ctctcagcca aatagctggc ttgctaagta     840
gaacactggt acttaggtga gggggacagg ggctgcttct ctctggagga tttgggctc     900 cggtgaccac caactttcc ctgagcagct tgtcactccc agaatccca cggctggcag     960 atggactagt gcacaactca gctgtggctg cacataataa atagaggata gatggtgggc    1020
cccagcccag cgatgtctgg cagtcaccca gagacactag ctaacggccc aggcttagtc    1080
ttgcctgggt gtgatcaggc agttctccaa aagtgcctga ctccatgaga agttttgttt    1140
gttctattga gcacagttcc tttctagatc cggggcaggg gatatctgga ggcatcttct    1200
tgcaacacct ccagttattg gaccactggg gctcgcccta tgcttgggat aggatggcct    1260
tgagtctcta agaggtcaag atccatgaaa acctctccaa ccagagttct gcttccaagt    1320
tgaaccccaa cacacctagc aaattagaac cacagcagaa ggggccccc cggatctggc    1380 tttccggcta ttgctagcaa ttgctagcaa ggggagtga ctctctgtcc attcaatcca    1440
ggccccgcgt gtccctcaaa caagaggcca cacaaatagg gtccgggcct cgatgctgac    1500
cctcatccac ttaagtgctc gatatccacg tgacatccac acccagaggg tcctggggtg    1560
gttgggtgac ccccagaatg caggcctagt aaccgagaca ttgaatgggg cagtgtccac    1620
```

```
aagggcggag gctattcctg tacatctggg cctacggagc cagcacccat cgccaaaact    1680
cttcatcctc ttcctcaatc tcgctttctc tctcgctttt ttttttttc ttcttcttt     1740
tttttttttt tttcaaaagg aggggagagg gggtaaaaaa atgctgcact gtgcggcgag   1800
gccggtgagt gagcgacgcg gagccaatca gcgcccgccg ttccgaaagt tgccttttat   1860
ggctcgagtg gccgctgtgg cgtcctataa aacccggcgg cgcaacgcgc agccactgtc   1920
gagtcgcgtc cacccgcgag cacagcttct ttgcagctcc ttcgttgccg gtccacaccc   1980
gccaccaggt aagcagggac gccgggccca gcgggccttc gctctctcgt ggctagtacc   2040
tcactgcagg gtcctgagga tcactcagaa cggacaccat gggcgggtgg agggtggtgc   2100
cgggccgcgg agcggacact ggcacagcca actttacgcc tagcgtgtag actctttgca   2160
gccacattcc cgcggtgtag acactcgtgg gcccgctccc gctcggtgcg tggggcttgg   2220
ggacacacta gggtcgcggt gtgggcattt gatgagccgg tgcggcttgc gggtgttaaa   2280
agccgtatta ggtccatctt gagagtacac agtattggga accagacgct acgatcacgc   2340
ctcaatggcc tctgggtctt tgtccaaacc ggtttgccta ttcggcttgc cgggcgggcg   2400
ggcgggcggg cgggcgcggc agggccggct cggccgggtg ggggctggga tgccactgcg   2460
cgtgcgctct ctatcactgg gcatcgaggc gcgtgtgcgc tagggaggga gctcttcctc   2520
tcccctctt cctagttagc tgcgcgtgcg tattgaggct gggagcgcgg ctgcccgggg    2580
ttgggcgagg gcggggccgt tgtccggaag gggcggggtc acagtggcac gggcgccttg   2640
tttgcgcttc ctgctgggtg tggtcgcctc ccgcgcgcgc acaagccgcc cgtcggcgca   2700
gtgtaggcgg agcttgcgcc cgtttgggga ggggcggag gtctggcttc ctgccctagg    2760
tccgcctccg ggccagcgtt tgcctttat ggtaataatg cggccggtct gcgcttcctt    2820
tgtcccctga gcttgggcgc gcgcccctg gcggctcgag cccgcggctt gccggaagtg    2880
ggcagggcgg cagcggctgc tcttggcggc cccgaggtga ctatagcctt cttttgtgtc   2940
ttgatagttc gcc                                                      2953

<210> SEQ ID NO 4
<211> LENGTH: 4164
<212> TYPE: DNA
<213> ORGANISM: Cricetulus griseus
<400> SEQUENCE: 4
aatgctgcac tgtgcggcta ggccggtgag tgagcggcgc ggagccaatc agcgctcgcc      60
gttccgaaag ttgcctttta tggctcgagt ggccgctgtg gcgtcctata aacccggcg     120
gcgcaacgcg cagccactgt cgagtccgcg tccacccgcg agcacaggcc tttcgcagct    180
ctttcttcgc cgctccacac ccgccaccag gtaagcaggg acaacaggcc cagccggcca    240
cagccctccc gtgggcagtg accgcgctgc agggtcgcgg gggacactcg gcgcggacac    300
cggggaaggc tggagggtgg tgccgggccg cggagcggac actttcagat ccaactttca    360
gtccagggtg tagacccttt acagccgcat tgccacggtg tagacaccgg tggacccgct    420
ctggctcaga gcacgcggct tggggggaacc cattagggtc gcagtgtggg cgctatgaga    480
gccgatgcag ctttcgggtg ttgaaccgta tctgcccacc ttgggggag acacaaggt     540
cgggagccaa acgccacgat catgccttgg tggcccatgg gtctttgtct aaaccggttt    600
gcccatttgg cttgccgggc gggcgggcgc ggcgggcccg gctcggccgg gtggggctg    660
ggttgccact gcgcttgcgc gctctatggc tgggtattgg ggcgcgtgca cgctggggag    720
```

```
ggagcccttc ctcttccccc tctcccaagt taaacttgcg cgtgcgtatt gagacttgga    780
gcgcggccac cggggttggg cgaggcgggc gccgttgtcc ggaaggggcg gggtcgcaga    840
ggattcgggg cgcctgctcg cgcttcctgc tgggtgtggt cgcctcccgc gcgcgcacta    900
gaccgcccgg cggggggggcg aaggcgggtc ttgcgcccgt ttggggaggg ggcggagacc   960
tggcttcctg ccgtggggcc gcctccggac cagcgtttgc ctcttatggt aataacgcgg   1020
ccggcctggg cttcatttgt cccctgagtt tgggcgcgcg ccccctggcg gcccgagacc   1080
gcggcttgcc ggaagtgggc agggcggcaa cggctgcgcc tagtggcccg ccagtgaccg   1140
cgaccctctt ttgtgccctg atatagttcg ccatggatga cgatatcgct gcgctcgttg   1200
tcgacaacgg ctccggcatg tgcaaagccg gcttcgcggg cgacgatgct ccccgggccg   1260
tcttcccatc catcgtgggc cgccctaggc accaggtagg tgacccttcc ctttgcgggt   1320
agcgatgctg gggttttcct ggggggagag gtgaccatat tgagaacatc gttcccctcc   1380
gcagggcgtg atggtgggca tgggccagaa ggactcctac gtgggtgacg aggcccagag   1440
caagagaggt attctgaccc tgaagtaccc cattgaacac ggcattgtca ccaactggga   1500
cgatatggag aagatctggc accacacctt ctacaacgag ctgcgtgtgg ccccccgagga  1560
gcaccctgtg ctgctcaccg aggccccccct gaaccccaag gccaaccgtg aaaagatgac   1620
ccaggtcagc agccagggtg gccacctcca tctttgccaa cttctcggcc acgcccttttc   1680
tcaattgtct ttcttctgcc gttctcccat aggactctct tctatgagct gagtctccct   1740
tggaactttg cagtttctgc ttttttcccccg atgaggtcct ttttttctct tgattgcctt  1800
tctgactagg tgttttaaac cctacggtgc tgtgggtgta ggtactaaca atgactcgtg   1860
tgacaaacct aatgaggctg gtgataagtg gccttggagt gtgtattcag tagatgcaca   1920
gtaggtttaa aatggagccc ctgtcctgag atttctccca gcacacttac cttagctgtg   1980
ttcttgcact ctgcatgtcc catatctgtc ctgacagtcc tacctgcctt gactacttgt   2040
ggcttttgga gtttgacaat gcctcatttt tctttataga tcatgtttga gaccttcaac   2100
accccagcca tgtacgtagc cattcaggct gtgctgtccc tgtatgcctc tggtcgtacc   2160
actggcattg tgatggactc cggagacggg gtcacccaca ctgtgcccat ctatgagggc   2220
tacgctctcc ctcatgccat cctgcgtctg gacctggctg gccgggacct gacagactac   2280
ctcatgaaga tcctgaccga gcgtggctac agctttacca ccacagctga gagggaaatt   2340
gtgcgtgaca tcaaagagaa gctgtgctat gttgccctgg acttcgagca ggagatggcc   2400
actgctgcat cctcttcctc cctggagaag agctatgagc tgcctgatgg ccaggtcatc   2460
accattggca atgagcggtt ccgttgcccct gaggctcttt tccagccttc cttcctgggt   2520
gagttgaagt gacctagttt cttcatctaa tggtgaccaa ctcttgatct tgagaccatg   2580
ctataagtct atcttttctct ttccctttttc cctcaggtat ggaatcctgt ggcatccacg  2640
aaactacatt caattccatc atgaagtgtg acgtcgacat ccgcaaagac ctctatgcca   2700
acacagtgct gtctggtggt accaccatgt acccaggcat tgctgaccgg atgcagaagg   2760
agatcactgc tctggctccc agcaccatga agatcaaggt gagctaagca tccttagcct   2820
tggacccatg atgggccctt ccaggtcaac cccttgactg tgggtaagac aggagtccag   2880
agcactcact atcactgtgt cttggcttct cagatcattg ctcctcctga gcgcaagtac   2940
tctgtgtgga tcggtggctc catcctggcc tcactgtcca ccttccagga gatgtggatc   3000
agcaagcagg agtacgatga gtccggcccc tccatcgtcc accgcaaatg cttctaggcg   3060
gactgttact gagctgtgtt ttacacccctt tcttgacaa aacctaactt gcgcagaaaa   3120
```

```
aaaaatgaga caacattggc atggctttgt ttttttgttt tgttttttta attttttta      3180 aaaaggtttt gtttttttt tttttgtgt tgttttggcg cttttgactc aggatttaaa       3240
aactggaacg gtgaaggcga cagcagtcgg ttggagcaaa catcccccaa agttctacaa     3300
tgtggctgag gactttgatt gcacattttt tttctttttt aagtcattcc aagtacccat    3360
gagatggcta caggaagtcc ctcaccctcc caaaagccat ccccattccc tagaaggga     3420 tggctgagtc cattccctga gtccacaccg gggaggtgac agcattgctt ctgtgtaaat    3480
tatggactcc caaatttttt ttaaatcttc cgccttaaaa cttcttttgt ttttaatttt   3540
ggatggtcaa ccatcgtggc ccctttttt tttttttttt tttgtccccc caacttgatg     3600
tatgaaggct tttggtctcc ctgggagtgg gttgaggtgt tgaggcagcc agggcttgcc    3660
tgtacactga cttgagacca gtttaataaa gtgcacacct tacaaacagt gctgcttgtt   3720
tgtggctttg ctagattctg ggtagcagcg gggaggggg tcactattac ctttgctcca    3780
agaggttcta gggtggtctg ggccttgcct agtagttttt agtgggagga cacaagcatc  3840
atgaccttta accagttatc acaaataccc tgtccattga gttctgaagt cttaattgtg   3900
tcttggttgg aagggtgtcc atcctgaatt gggaataccc cctgggccaa gttgggttcc   3960
tgcagcaaac aaccctgtaa tctcaaccttc cctctacctt tgtgggaagc aggaatcctg   4020
ttgggagggt agctttactg cctttgagtt ctgcaagaca gtgggaagta aaagcagtct    4080
cggttctctt gctttaccag atacatgatc acaaagttta agggtgttaa ggctccccag  4140
gcatgggtat ctttccccgg tacc                                           4164

<210> SEQ ID NO 5
<211> LENGTH: 2011
<212> TYPE: DNA
<213> ORGANISM: Homo sapiens

<400> SEQUENCE: 5
gagctctgtc tcttggccag ctgaatggag gcccagcggc aacacaggtc ctgcctgggg     60
atcaggtctg ctctgcaccc caccttgctg cctggagccg cccacctgac aacctctcat   120
ccctgctctg tagatccggt cccatcccca ctgcccaccc caccccccca gcactccacc    180
cagttcaacg ttccacgaac ccccagaacc agccctcatc aacaggcagc aagaagggcc    240
ccccgcccat cgccccacaa cgccagccgg gtgaactgta gcgttggcag gtcctgaggc    300
agctgaaaga tacaaggcca gggacaggac agtcccatcc ccaggaggca gggagtatac    360
aggctgggga agttgccct tgcgtggggt ggtgatggag gaggctcagc aagtcttctg    420
gactgtgaac ctgtgtctgc cactgtgtgc tgggtggtgg tcatctttcc caccaggctg    480
tggcctctgc aaccttcaag ggaggagcag gtcccattgg ctgagcacag ccttgtacgt    540
gaactgaaca agcagcctcc ttcctggcca caggttccat gtccttatat ggactcatct    600
ttgcctattg cgacacacac tcaatgaaca cctactacgc gctgcaaaga gccccgcagg     660
cctgaggtgc ccccacctca ccactcttcc tattttgtg taaaaatcca gcttcttgtc    720
accacctcca aggaggggga ggaggaggaa ggcaggttcc tctaggctga gccgaatgcc    780
cctctgtggt cccacgccac tgatcgctgc atgcccacca cctgggtaca cacagtctgt   840
gattcccgga gcagaacgga ccctgcccac ccggtcttgt gtgctactca gtggacagac    900
ccaaggcaag aaagggtgac aaggacaggt tcttcccagg ctggctttga gttcctagca   960 ccgcccgcc cccaatcctc tgtggcacat ggagtcttgg tccccagagt cccccagcgg    1020
```

```
cctccagatg gtctgggagg gcagttcagc tgtggctgcg catagcagac atacaacgga    1080
cggtgggccc agacccaggc tgtgtagacc cagcccccc gccccgcagt gcctaggtca    1140
cccactaacg ccccaggcct ggtcttggct gggcgtgact gttaccctca aaagcaggca    1200
gctccagggt aaaaggtgcc ctgccctgta gagcccactt ccttcccagg gctgcggctg    1260
ggtaggtttg tagccttcat cacgggccac ctccagccac tggaccgctg gccctgccc     1320 tgtcctgggg agtgtggtcc tgcgactcta atggccgcaa gccacctgac tcccccaaca    1380
ccacactcta cctctcaagc ccaggtctct ccctagtgac ccaccagca catttagcta    1440 gctgagcccc acagccagag gtcctcaggc cctgctttca gggcagttgc tctgaagtcg    1500
gcaaggggga gtgactgcct ggccactcca tgccctccaa gagctccttc tgcaggagcg    1560
tacagaaccc agggccctgg cacccgtgca gaccctggcc cacccacct gggcgctcag     1620 tgcccaagag atgtccacac ctaggatgtc ccgcggtggg tggggggccc gagagacggg    1680
caggccgggg gcaggcctgg ccatgcgggg ccgaaccggg cactgcccag cgtggggcgc    1740
gggggccacg gcgcgcgccc cagcccccg ggcccagcac ccaaggcgg ccaacgccaa      1800 aactctccct cctcctcttc ctcaatccgc ctctcgctct ttttttttt cgcaaaagga    1860 ggggagaggg ggtaaaaaaa tgctgcactg tcggcgaagc cggtgagtga gcggcgcggg    1920
gccaatcgcg tgcgccgttc cgaaagttgc cttttatggc tcgagcggcc gcggcggcgc    1980
cctataaaac ccagcggcgc gacgcgccac c                                   2011

<210> SEQ ID NO 6
<211> LENGTH: 1278
<212> TYPE: DNA
<213> ORGANISM: Gallus gallus

<400> SEQUENCE: 6
tcgaggtgag ccccacgttc tgcttcactc tccccatctc ccccccctcc ccaccccaa      60 ttttgtattt atttattttt taattatttt gtgcagcgat ggggcgggg gggggggg      120 cgcgcgccag gcggggcggg gcggggcgag gggcggggcg gggcgaggcg gagaggtgcg    180
gcggcagcca atcagagcgg cgcgctccga aagtttcctt ttatggcgag gcggcggcgg    240
cggcggccct ataaaagcg aagcgcgcg cgggcgggag tcgctgcgtt gccttcgccc     300
cgtgccccgc tccgcgccgc ctcgcgccgc ccgccccggc tctgactgac cgcgttactc    360
ccacaggtga gcgggcggga cggcccttct cctccgggct gtaattagcg cttggtttaa    420
tgacggctcg tttcttttct gtggctgcgt gaaagcctta aagggctccg ggagggccct    480
ttgtgcgggg gggagcggct cgggggggtgc gtgcgtgtgt gtgtgcgtgg ggagcgccgc    540
gtgcggcccg cgctgcccgg cggctgtgag cgctgcgggc gcggcgcggg gctttgtgcg    600
ctccgcgtgt gcgcgagggg agcgcggccg ggggcggtgc cccgcggtgc ggggggggctg    660 cgagggggaac aaaaggctgcg tgcggggtgt gtgcgtgggg gggtgagcag ggggtgtggg   720
cgcggcggtc gggctgtaac ccccccctgc acccccctcc ccgagttgct gagcacggcc    780
cggcttcggg tgcggggctc cgtgcggggc gtggcgcggg gctcgccgtg ccgggcgggg    840
ggtggcggca ggtgggggtg ccgggcgggg cggggccgcc tcgggccggg gagggctcgg    900
gggaggggcg cggcggcccc ggagcgccgg cggctgtcga ggcgcggcga gccgcagcca    960
ttgcctttta tggtaatcgt gcgagagggc gcagggactt cctttgtccc aaatctggcg    1020
gagccgaaat ctgggaggcg ccgccgcacc cctctagcg ggcgcgggcg aagcggtgcg     1080
gcgccggcag gaaggaaatg gcggggagg gccttcgtgc gtcgccgcgc cgccgtcccc    1140
```

```
ttctccatct ccagcctcgg ggctgccgca gggggacggc tgccttcggg ggggacgggg    1200
cagggcgggg ttcggcttct ggcgtgtgac cggcggggtt tatatcttcc cttctctgtt    1260
cctccgcagc cagccatg                                                   1278

<210> SEQ ID NO 7
<211> LENGTH: 3668
<212> TYPE: DNA
<213> ORGANISM: Artificial Sequence
<220> FEATURE:
<223> OTHER INFORMATION: longer beta-actin promoter sequence from CHO
      cells

<400> SEQUENCE: 7
cttcctccac ttcctcttcc cccaccccca ccctgttttc tgtgctctct cctgtctgca      60
catcaaactc aacaactcag gcatccccct ctggccctgc catcttctca gggtcctctc     120
cttcttcatg gctgaggaca cccaggccag gcagcctcgt attcatccaa cagaacagag     180
cccctcagtg tgtgtgtagt gggaggaagt gggggtgttg gagcccctca aagggctgtc     240
ttgtttgatg ttgtggggt tggggcagt gctgagttaa gactagcctg aatagcacca     300
tgactgtctg catagctact caggaagctg aggcaggaag atgaggagtt ggaggccagc     360
ctgggctata tagggagaca ctatttcaaa caaacaggag gagctgggca tggtggcata     420
tgcctttaat cataacactc aggaagtaca ggcaggagga ttaggagttc aaggttactt     480
gggctacata gagaatttga ggccagtcta ggctgcgtga cactgtcaa aaaaacaaa     540 agaacaaaac ccccacacac aaaaaaaact cccaacaaa ccagaaaat caatctctct     600 ctcgttatct cttgctttct ctcatgccta agagaacact ggaaaatggc cattgcagac     660
cgggaccaag acagaaccat aagccagtgg gatagatcag aaatgttcca gaggtgggat     720
ggggccagag tgcctgcccc ttgaaccgtc ccagggacca gaggtgacaa agtggcaaca     780
caggtcctgc ctgggaatct ggtctgctcc tacttagtaa agctgcctgg tgtcacacaa     840
gaggccccca ttattcctg caccctggt ggtaggtggc gtcttctccc ctgcagccac     900
caggctcccc tgagaacact gccggcagtc ctcattgaca ggcagtattc gctctgcccc     960
acccccacct gtgaattgca gggctggcag gtcctcaggc agctggcaaa ccgcctgaac    1020
aactgagaga tacagggcca gggccagggc agtcccgtcc cccggaggca gggaggggac    1080
gtgctgggaa agttctctct ctcaggccca ggttggtgac tgcagaaggc ttctgtcaaa    1140
tctcttttgt gggaaccaca gagtagccct gaacgtgggg gtgtgcttcc agtatactct    1200
ggggtcaccc tttccatact ggaggcctct gcaacttcaa aatgtctctgc taccaaccta    1260 gcacaaggaa gttggtccag cctccccacg cagggccact gctgcagtcc atatatggac    1320
taagccttcc ttggtttcaa cacctacact cactgagccc ctactatgtg tatgcagagc    1380
cgagacaggc ccgagcatct catctgaagc acccttcttg cctaaattca gttttctgtc    1440
actttctccc aggaggtgtg tgtccctcta agctaagcca ggggtccctc accctgccc    1500 cactcccatc cctagtgtag gtatcagctg aagagcttcc tgagcagaac actcttgggt    1560
gctgacattt tgataaatag gcccatgttt aggagagcag gggtccgggg gcgggagatc    1620
ttctctggtg gattgagggc tccaagaact actctttgag cacgctgccc ctcccagagt    1680
ccccacagcc tccagatgga ctagaacaca gttcggctgt ggctgcacat aactaacaga    1740
ggatagatgg tgggtcccag cccaacagtg cctggcaatc acccagagcc accagctaac    1800
ggccttggct tagttttttg cctgggtgtg atcaggcagc cctccaaaac tgcccggact    1860
```

```
ccatgacaag ttttgcttgt tctatagagc acagttcctt tctaggtctg gggcaaggga    1920
catcgggaga catcttcctg caacagctcc agtcactgga ccaccaggct cgccctgtct    1980
ttggtgtgtg gccctgagtc tcctaagtgg cccaaacctg tgaagacccc tccaaccaca    2040
gttttgcttc taaattgtac cccaacacac ctagcaaatt gaaacccccac cagaagtccc   2100 ccagatctgg ctttccggct attgctggca aggggagtg actcccgcc cattcaatcc      2160 aggccccgcg tgttcctcaa acaagaagcc acgtaaacat aaaccgagcc tccatgctga    2220
cccttgccca tcgaggtact caatgttcac gtgatatcca cacccagagg gtcctggggt    2280
gggtgcatga gccccagaat gcaggcttga taaccgagac cctgaatcgg gcagtgtcca    2340
caagggcgga ggcccagtca tgcatgttcg ggcctatggg gccagcaccc aacgccaaaa    2400
ctctccatcc tcttcctcaa tctcggcttt ctctctctct ctctttttt ttttttattt    2460 tttttttttg caaaggagg ggagagggg taaaaaaatg ctgcactgtg cggctaggcc      2520
ggtgagtgag cggcgcggag ccaatcagcg ctcgccgttc cgaaagttgc cttttatggc    2580
tcgagtggcc gctgtggcgt cctataaaac ccggcggcgc aacgcgcagc cactgtcgag    2640
tccgcgtcca cccgcgagca caggcctttc gcagctcttt cttcgccgct ccacacccgc    2700
caccaggtaa gcaggacaa caggcccagc cggccacagc cctcccgtgg gcagtgaccg     2760
cgctgcaggg tcgcggggga cactcggcgc ggacaccggg gaaggctgga gggtggtgcc    2820
gggccgcgga gcggacactt tcagatccaa ctttcagtcc agggtgtaga ccctttacag    2880
ccgcattgcc acggtgtaga caccggtgga cccgctctgg ctcagagcac gcggcttggg    2940
ggaacccatt agggtcgcag tgtgggcgct atgagagccg atgcagcttt cgggtgttga    3000
accgtatctg cccaccttgg ggggaggaca caaggtcggg agccaaacgc cacgatcatg    3060
ccttggtggc ccatgggtct ttgtctaaac cggtttgccc atttggcttg ccgggcgggc    3120
gggcgcggcg ggcccggctc ggccgggtgg gggctgggtt gccactgcgc ttgcgcgctc    3180 tatgctggg tattggggcg cgtgcacgct ggggagggag ccttcctct tccccctctc      3240 ccaagttaaa cttgcgcgtg cgtattgaga cttggagcgc ggccaccggg gttgggcgag    3300
ggcggggccg ttgtccggaa ggggcggggt cgcagcggct tcggggcgcc tgctcgcgct    3360
tcctgctggg tgtggtcgcc tcccgcgcgc gcactagccg cccgccggcg gggcgaaggc    3420
ggggcttgcg cccgtttggg gaggggggcgg aggcctggct tcctgccgtg gggccgcctc   3480
cggaccagcg tttgcctctt atggtaataa cgccggccgc ctgggcttcc tttgtcccct    3540
gagtttgggc gcgcgccccc tggcggcccg aggccgcggc ttgccggaag tgggcagggc    3600
ggcagcggct gcgcctagtg gcccgctagt gaccgcgacc ctcttttgtg ccctgatata    3660
gttcgccg                                                            3668
```

<210> SEQ ID NO 8
<211> LENGTH: 19
<212> TYPE: DNA
<213> ORGANISM: Artificial Sequence
<220> FEATURE:
<223> OTHER INFORMATION: forward primer for beta-actin

<400> SEQUENCE: 8
gctctttctt cgccgctcc    19

<210> SEQ ID NO 9
<211> LENGTH: 19
<212> TYPE: DNA

```
<213> ORGANISM: Artificial Sequence
<220> FEATURE:
<223> OTHER INFORMATION: reverse primer for beta-actin

<400> SEQUENCE: 9
accaccctcc agccttccc                                                    19

<210> SEQ ID NO 10
<211> LENGTH: 20
<212> TYPE: DNA
<213> ORGANISM: Artificial Sequence
<220> FEATURE:
<223> OTHER INFORMATION: forward primer for EF-1

<400> SEQUENCE: 10
gaacgcaggt gttgtgaaaa                                                   20

<210> SEQ ID NO 11
<211> LENGTH: 17
<212> TYPE: DNA
<213> ORGANISM: Artificial Sequence
<220> FEATURE:
<223> OTHER INFORMATION: reverse primer for EF-1

<400> SEQUENCE: 11
ctcggcagcc tccttct                                                      17

<210> SEQ ID NO 12
<211> LENGTH: 16
<212> TYPE: DNA
<213> ORGANISM: Artificial Sequence
<220> FEATURE:
<223> OTHER INFORMATION: forward primer for rpS21

<400> SEQUENCE: 12
gtggacctgt acgtgc                                                       16

<210> SEQ ID NO 13
<211> LENGTH: 20
<212> TYPE: DNA
<213> ORGANISM: Artificial Sequence
<220> FEATURE:
<223> OTHER INFORMATION: reverse primer for rpS21

<400> SEQUENCE: 13
ttctcacttt tatttatgac                                                   20

<210> SEQ ID NO 14
<211> LENGTH: 21
<212> TYPE: DNA
<213> ORGANISM: Artificial Sequence
<220> FEATURE:
<223> OTHER INFORMATION: forward primer for ferritin

<400> SEQUENCE: 14
cgccagaact accaccagga c                                                 21

<210> SEQ ID NO 15
<211> LENGTH: 20
<212> TYPE: DNA
<213> ORGANISM: Artificial Sequence
<220> FEATURE:
<223> OTHER INFORMATION: reverse primer for ferritin

<400> SEQUENCE: 15
ttcagagcca catcatcccg                                                   20
```

<210> SEQ ID NO 16
<211> LENGTH: 21
<212> TYPE: DNA
<213> ORGANISM: Artificial Sequence
<220> FEATURE:
<223> OTHER INFORMATION: forward primer for galectin

<400> SEQUENCE: 16
tggtcgcaag caacctgaat c                                              21

<210> SEQ ID NO 17
<211> LENGTH: 20
<212> TYPE: DNA
<213> ORGANISM: Artificial Sequence
<220> FEATURE:
<223> OTHER INFORMATION: reverse primer for galectin

<400> SEQUENCE: 17
ttgaagtcac cgtctgccgc                                                20

<210> SEQ ID NO 18
<211> LENGTH: 17
<212> TYPE: DNA
<213> ORGANISM: Artificial Sequence
<220> FEATURE:
<223> OTHER INFORMATION: forward M13 primer

<400> SEQUENCE: 18
gttttcccag tcacgac                                                   17

<210> SEQ ID NO 19
<211> LENGTH: 14
<212> TYPE: DNA
<213> ORGANISM: Artificial Sequence
<220> FEATURE:
<223> OTHER INFORMATION: alu repeat SAGE tag

<400> SEQUENCE: 19
catggaagca gaat                                                      14

<210> SEQ ID NO 20
<211> LENGTH: 14
<212> TYPE: DNA
<213> ORGANISM: Artificial Sequence
<220> FEATURE:
<223> OTHER INFORMATION: Mitochondrial COX I SAGE tag

<400> SEQUENCE: 20
catgcaggag cttc                                                      14

<210> SEQ ID NO 21
<211> LENGTH: 14
<212> TYPE: DNA
<213> ORGANISM: Artificial Sequence
<220> FEATURE:
<223> OTHER INFORMATION: Ribosomal Protein S21 SAGE tag

<400> SEQUENCE: 21
catgggggag cgtt                                                      14

<210> SEQ ID NO 22
<211> LENGTH: 14
<212> TYPE: DNA
<213> ORGANISM: Artificial Sequence
<220> FEATURE:

-continued

```
<223> OTHER INFORMATION: Mitochondrial COX II SAGE tag

<400> SEQUENCE: 22
catggtactg acac                                                    14

<210> SEQ ID NO 23
<211> LENGTH: 14
<212> TYPE: DNA
<213> ORGANISM: Artificial Sequence
<220> FEATURE:
<223> OTHER INFORMATION: GAPDH SAGE tag

<400> SEQUENCE: 23
catggcctcc aagg                                                    14

<210> SEQ ID NO 24
<211> LENGTH: 14
<212> TYPE: DNA
<213> ORGANISM: Artificial Sequence
<220> FEATURE:
<223> OTHER INFORMATION: Mitochondrial ATPase SAGE tag

<400> SEQUENCE: 24
catgataata cgta                                                    14

<210> SEQ ID NO 25
<211> LENGTH: 14
<212> TYPE: DNA
<213> ORGANISM: Artificial Sequence
<220> FEATURE:
<223> OTHER INFORMATION: B-1 repeat SAGE tag

<400> SEQUENCE: 25
catgccttta atcc                                                    14

<210> SEQ ID NO 26
<211> LENGTH: 14
<212> TYPE: DNA
<213> ORGANISM: Artificial Sequence
<220> FEATURE:
<223> OTHER INFORMATION: Mitochondrial Cytochrome B SAGE tag

<400> SEQUENCE: 26
catgaatcgg aggc                                                    14

<210> SEQ ID NO 27
<211> LENGTH: 14
<212> TYPE: DNA
<213> ORGANISM: Artificial Sequence
<220> FEATURE:
<223> OTHER INFORMATION: EF-1 SAGE tag

<400> SEQUENCE: 27
catgaggcag acag                                                    14

<210> SEQ ID NO 28
<211> LENGTH: 14
<212> TYPE: DNA
<213> ORGANISM: Artificial Sequence
<220> FEATURE:
<223> OTHER INFORMATION: Galectin SAGE tag

<400> SEQUENCE: 28
catggcggca gacg                                                    14
```

```
<210> SEQ ID NO 29
<211> LENGTH: 14
<212> TYPE: DNA
<213> ORGANISM: Artificial Sequence
<220> FEATURE:
<223> OTHER INFORMATION: Alu repeat SAGE tag

<400> SEQUENCE: 29
catggtggct caca                                                     14

<210> SEQ ID NO 30
<211> LENGTH: 14
<212> TYPE: DNA
<213> ORGANISM: Artificial Sequence
<220> FEATURE:
<223> OTHER INFORMATION: Ferritin heavy chain SAGE tag

<400> SEQUENCE: 30
catgttggct gccg                                                     14

<210> SEQ ID NO 31
<211> LENGTH: 14
<212> TYPE: DNA
<213> ORGANISM: Artificial Sequence
<220> FEATURE:
<223> OTHER INFORMATION: unknown SAGE tag

<400> SEQUENCE: 31
catgccctgt gccg                                                     14

<210> SEQ ID NO 32
<211> LENGTH: 14
<212> TYPE: DNA
<213> ORGANISM: Artificial Sequence
<220> FEATURE:
<223> OTHER INFORMATION: Ribosomal protein L41 SAGE tag

<400> SEQUENCE: 32
catgagagcg aagt                                                     14

<210> SEQ ID NO 33
<211> LENGTH: 14
<212> TYPE: DNA
<213> ORGANISM: Artificial Sequence
<220> FEATURE:
<223> OTHER INFORMATION: Mitochondrial Dehydrogenase SAGE tag

<400> SEQUENCE: 33
catgaggagg ccta                                                     14

<210> SEQ ID NO 34
<211> LENGTH: 14
<212> TYPE: DNA
<213> ORGANISM: Artificial Sequence
<220> FEATURE:
<223> OTHER INFORMATION: beta-actin SAGE tag

<400> SEQUENCE: 34
catgccctga gtcc                                                     14

<210> SEQ ID NO 35
<211> LENGTH: 26
<212> TYPE: DNA
<213> ORGANISM: Artificial Sequence
<220> FEATURE:
<223> OTHER INFORMATION: forward primer for amplifying beta-actin
      promoter containing intron 1
```

<400> SEQUENCE: 35
aggcccagct tgggaccaag acagaa                                          26

<210> SEQ ID NO 36
<211> LENGTH: 27
<212> TYPE: DNA
<213> ORGANISM: Artificial Sequence
<220> FEATURE:
<223> OTHER INFORMATION: reverse primer for amplifying beta-actin
      promoter containing intron 1.

<400> SEQUENCE: 36
cgcggatccg gcgaactata tcagggc                                         27

<210> SEQ ID NO 37
<211> LENGTH: 1884
<212> TYPE: DNA
<213> ORGANISM: Artificial Sequence
<220> FEATURE:
<223> OTHER INFORMATION: cDNA enoding acid-sphingomyelinase

<400> SEQUENCE: 37

| | |
|---|---|
| atggcccgct acggagcgtc actccgccag agctgcccca ggtccggccg ggagcaggga | 60 |
| caagacggga ccgccggagc ccccggactc ctttggatgg gcctggcgct ggcgctggcg | 120 |
| ctggcgctgg ctctgtctga ctctcgggtt ctctgggctc cggcagaggc tcaccctctt | 180 |
| tctccccaag gccatcctgc caggttacat cgcatagtgc cccggctccg agatgtcttt | 240 |
| gggtggggga acctcacctg cccaatctgc aaaggtctat tcaccgccat caacctcggg | 300 |
| ctgaagaagg aacccaatgt ggctcgcgtg ggctccgtgg ccatcaagct gtgcaatctg | 360 |
| ctgaagatag caccacctgc cgtgtgccaa tccattgtcc acctctttga ggatgacatg | 420 |
| gtggaggtgt ggagacgctc agtgctgagc ccatctgagg cctgtggcct gctcctgggc | 480 |
| tccacctgtg gcactgggca tttttctca tcttggaaca tctcttttgcc tactgtgccg | 540 |
| aagccgcccc ccaaaccccc tagccccccca gccccaggtg cccctgtcag ccgcatcctc | 600 |
| ttcctcactg acctgcactg ggatcatgac tacctggagg gcacggaccc tgactgtgca | 660 |
| gacccactgt gctgccgccg gggttctggc ctgccgcccg catcccggcc aggtgccgga | 720 |
| tactgggcg aatacagcaa gtgtgacctg ccctgaga ccctggagag cctgttgagt | 780 |
| gggctgggcc cagccggccc ttttgatatg gtgtactgga caggagacat ccccgcacat | 840 |
| gatgtctggc accagactcg tcaggaccaa ctgcgggccc tgaccaccgt cacagcactt | 900 |
| gtgaggaagt tcctggggcc agtgccagtt taccctgctg tgggtaacca tgaaagcaca | 960 |
| cctgtcaata gcttccctcc cccttcatt gagggcaacc actcctcccg ctggctctat | 1020 |
| gaagcgatgg ccaaggcttg ggagccctgg ctgcctgccg aagccctgcg caccctcaga | 1080 |
| attgggggt tctatgctct tccccatac cccggtctcc gcctcatctc tctcaatatg | 1140 |
| aattttttgt cccgtgagaa cttctggctc ttgatcaact ccacggatcc cgcaggacag | 1200 |
| ctccagtggc tggtgggga gcttcaggct gctgaggatc gaggagacaa agtgcatata | 1260 |
| attggccaca ttccccccagg gcactgtctg aagagctgga gctggaatta ttaccgaatt | 1320 |
| gtagccaggt atgagaacac cctggctgct cagttctttg ccacactca tgtggatgaa | 1380 |
| tttgaggtct tctatgatga agagactctg agccggccgc tggctgtagc cttcctggca | 1440 |
| cccagtgcaa ctacctacat cggccttaat cctggttacc gtgtgtacca aatagatgga | 1500 |
| aactactccg ggagctctca cgtggtcctg gaccatgaga cctacatcct gaatctgacc | 1560 |

```
caggcaaaca taccgggagc cataccgcac tggcagcttc tctacagggc tcgagaaacc    1620
tatgggctgc ccaacacact gcctaccgcc tggcacaacc tggtatatcg catgcggggc    1680
gacatgcaac ttttccagac cttctggttt ctctaccata agggccaccc accctcggag    1740
ccctgtggca cgccctgccg tctggctact ctttgtgccc agctctctgc ccgtgctgac    1800
agccctgctc tgtgccgcca cctgatgcca gatgggagcc tcccagaggc ccagagcctg    1860
tggccaaggc cactgttttg ctga                                           1884
```

<210> SEQ ID NO 38
<211> LENGTH: 2859
<212> TYPE: DNA
<213> ORGANISM: Artificial Sequence
<220> FEATURE:
<223> OTHER INFORMATION: cDNA encoding alpha-glucosidase.

<400> SEQUENCE: 38

```
atgggagtga ggcacccgcc ctgctcccac cggctcctgg ccgtctgcgc cctcgtgtcc      60
ttggcaaccg ctgcactcct ggggcacatc ctactccatg atttcctgct ggttccccga     120
gagctgagtg gctcctcccc agtcctggag gagactcacc cagctcacca gcagggagcc     180
agcagaccag gccccgggga tgcccaggca caccccggcc gtcccagagc agtgcccaca     240
cagtgcgacg tccccccccaa cagccgcttc gattgcgccc ctgacaaggc catcacccag     300
gaacagtgcg aggcccgcgg ctgctgctac atccctgcaa agcaggggct gcagggagcc     360
cagatggggc agccctggtg cttcttccca cccagctacc ccagctacaa gctggagaac     420
ctgagctcct ctgaaatggg ctacacggcc accctgaccc gtaccacccc caccttcttc     480
cccaaggaca tcctgaccct gcggctggac gtgatgatgg agactgagaa ccgcctccac     540
ttcacgatca agatccagc taacaggcgc tacgaggtgc ccttggagac ccgcgtgtc      600 cacagccggg caccgtcccc actctacagc gtggagttct ctgaggagcc cttcggggtg     660
atcgtgcacc ggcagctgga cggccgcgtg ctgctgaaca cgacggtggc cccctgttc      720 tttgcggacc agttccttca gctgtccacc tcgctgccct cgcagtatat cacaggcctc     780
gccgagcacc tcagtcccct gatgctcagc accagctgga ccaggatcac cctgtggaac     840
cgggaccttg cgcccacgcc cggtgcgaac ctctacgggt ctcacccttt ctacctggcg     900
ctggaggacg gcgggtcggc acacggggtg ttcctgctaa acagcaatgc catggatgtg     960
gtcctgcagc cgagccctgc ccttagctgg aggtcgacag gtgggatcct ggatgtctac    1020
atcttcctgg gcccagagcc caagagcgtg gtgcagcagt acctggacgt tgtgggatac    1080
ccgttcatgc cgccatactg gggcctgggc ttccacctgt gccgctgggg ctactcctcc    1140
accgctatca cccgccaggt ggtggagaac atgaccaggg cccacttccc cctggacgtc    1200
caatggaacg acctggacta catggactcc cggagggact tcacgttcaa caaggatggc    1260
ttccgggact ccggccat ggtgcaggag ctgcaccagg gcggccggcg ctacatgatg    1320
atcgtggatc ctgccatcag cagctcgggc cctgccggga gctacaggcc ctacgacgag    1380
ggtctgcgga gggggttttt catcaccaac gagaccggcc agccgctgat tgggaaggta    1440
tggcccgggt ccactgcctt ccccgacttc accaaccca cagccctggc ctggtgggag    1500
gacatggtgg ctgagttcca tgaccaggtg cccttcgacg gcatgtggat tgacatgaac    1560
gagccttcca acttcatcag gggctctgag gacggctgcc ccaacaatga gctgagaac    1620 ccaccctacg tgcctggggt ggttgggggg acctccagg cggccaccat ctgtgcctcc    1680
```

```
agccaccagt ttctctccac acactacaac ctgcacaacc tctacggcct gaccgaagcc      1740
atcgcctccc acagggcgct ggtgaaggct cgggggacac gcccatttgt gatctcccgc      1800
tcgacctttg ctggccacgg ccgatacgcc ggccactgga cggggacgt gtggagctcc       1860 tgggagcagc tcgcctcctc cgtgccagaa atcctgcagt ttaacctgct gggggtgcct      1920
ctggtcgggg ccgacgtctg cggcttcctg ggcaacacct cagaggagct gtgtgtgcgc      1980
tggacccagc tgggggcctt ctaccccttc atgcggaacc acaacagcct gctcagtctg      2040
ccccaggagc cgtacagctt cagcgagccg gcccagcagg ccatgaggaa ggccctcacc      2100
ctgcgctacg cactcctccc ccacctctac acgctgttcc accaggccca cgtcgcgggg      2160
gagaccgtgg cccggcccct cttcctggag ttccccaagg actctagcac ctggactgtg      2220
gaccaccagc tcctgtgggg ggaggccctg ctcatcaccc cagtgctcca ggccgggaag      2280
gccgaagtga ctggctactt ccccttgggc acatggtacg acctgcagac ggtgccaata      2340
gaggcccttg gcagcctccc acccccacct gcagctcccc gtgagccagc catccacagc      2400
gaggggcagt gggtgacgct gccggccccc ctggacacca tcaacgtcca cctccgggct      2460
gggtacatca tccccctgca gggccctggc ctcacaacca cagagtcccg ccagcagccc      2520
atggccctgg ctgtggccct gaccaagggt ggagaggccc gagggagct gttctgggac       2580 gatggagaga gcctggaagt gctggagcga ggggcctaca cacaggtcat cttcctggcc      2640
aggaataaca cgatcgtgaa tgagctggta cgtgtgacca gtgagggagc tggcctgcag      2700
ctgcagaagg tgactgtcct gggcgtggcc acggcgcccc agcaggtcct ctccaacggt      2760
gtccctgtct ccaacttcac ctacagcccc gacaccaagg tcctggacat ctgtgtctcg      2820
ctgttgatgg gagagcagtt tctcgtcagc tggtgttaa                             2859

<210> SEQ ID NO 39
<211> LENGTH: 1958
<212> TYPE: DNA
<213> ORGANISM: Artificial Sequence
<220> FEATURE:
<223> OTHER INFORMATION: Hamster rpS21 promoter

<400> SEQUENCE: 39
gatcaacatt tacgctggct gttttaatga gagcaccggt cttgggtcac ctcactgtca        60
cattggatga ggacccagta agtgctgaga gccgcagatg tagccggtgt gggtgaatgc       120
tgggctggtg tctgctggtc aaggtaccag aggctgcctc agcttcctca gagggacaaa       180
gggtcattaa cactgaggag gcttgtttat tagtttactc ttttctttcc acctaaaagt       240
ttgagctttt ctattagtgc tacaagtatg catcatggtc tgcttctcgt gaaggttttg       300
agcagatgga acacattcta tgaaaacccc tatcacaacc ctgtctacta attctaaact       360
ctgagtcagt cctgggtcag tttcaacggg ctgttctttc tctcattagt ggccatattc       420
ccttgctgtt ggatttggca gtctctgagt ggataccaga aaatacgatt ttttcctttg       480
ttgtgggctt catgctgcct ttgtgttccg ttttttttt tttgggggg gggatgtggt         540 ggagttattg ggtaatactt tgacccttgc aggccctgtt tttatgatgt taggggggcc      600
taggcattgt tcagggcagt tactggaggc tagacctttc tcaacactct aacccagtgc      660
tatgtgcact aaacttttc acctgtttcc agtccctgcc ctttttagga ctgctgaatt       720
tgctgagtag agctactgca aatttctggg gttttccttg gccactttct ccttactggc      780
actctgggtg tgctccatct ctggccacta aagagacctt cagggttcaa ctcaacacac      840
acaggtgcag ctctcaaagc taaaacacaa acaaaccacc cttgtacaca ggcctcatgg      900
```

-continued

```
ccttccaagg gcagtggcta tggttcttgt ttctgatgca cagaaagggt ctagtggaaa      960
ttccagacac aatgcccaca cctgctttcc caggcgtgag gagggtttca gcagacctca     1020
tgacagtcct gggaaggtgt cgggtgcgcg tggcagggag gggagagctc tccccaagat     1080
catttaactg ggtgtgcaca cctgaggcac cagtctgccc agagagacat caggtgcaca     1140
gttctacaga taagcgagac aagcggtccc tatgtgaaga atgtaacggt aggaaaacca     1200
acagtgtaga ctgggagtct tgtgtccggg ctggtttgca gcctcttcaa caggggctg     1260 cctgagcgtt aggggcattt tcctcctggt ttttaaagat tttatttgtt atgtagacag     1320
tgtactgcac cctctgggca gactcacaac actgggcggc cggatgccgt gctggccaga     1380
gcaggagagg gcagggcctg ggtggagacg ccgcagggga gcgcgccggc ccggacgcct     1440
ggctggtctc ggcggttccc actggactgc cgctctgctg acaccgtgc ccgcctccct     1500 ccgccgcgac tggcggcggc ttccggggag cgatttccag gtgcaggtct ggggtgtcgg     1560
cgtccccgca ggcgagccgg ctccttcga cgtccttcct atcccgcgcc ccgccgccc     1620 cccgccgccc cctcaacctc aagcagggga gacccggccg gggcgggca cgaagagcgc     1680 ggcggctcct gctgtgggcg gagctctcct gctatgggcg gagctggggg cggagccgcc     1740
ttggtagggt agagccaggc tccagtgtct gagcctttgt gcggaagagc cggggcttct     1800
ttgcaccgga agcggaagaa aagactccca agccggcctc cggaacggtg gatacgagca     1860
tcgtgacccg gaagtattca ccacacgcac cgcccctccc gcccaagaga gctgcctggg     1920
gacgacccac ttcctttctg cgctccgctg gcctagag                            1958
```

```
<210> SEQ ID NO 40
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
agctctaata cgactcacta tagggc                                            26

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ctctaggcca gcggagcgca g                                                 21
```